(12) United States Patent
Gelbart et al.

(10) Patent No.: US 9,750,569 B2
(45) Date of Patent: Sep. 5, 2017

(54) MEDICAL DEVICE FOR USE IN BODILY LUMENS, FOR EXAMPLE AN ATRIUM

(71) Applicant: KARDIUM INC., Burnaby (CA)

(72) Inventors: Daniel Gelbart, Vancouver (CA); Douglas Wayne Goertzen, New Westminster (CA); Fernando Luis de Souza Lopes, Delta (CA)

(73) Assignee: KARDIUM INC., Burnaby (CA)

( * ) Notice: Subject to any disclaimer, the term of this patent is extended or adjusted under 35 U.S.C. 154(b) by 366 days.

(21) Appl. No.: 14/521,692

(22) Filed: Oct. 23, 2014

(65) Prior Publication Data

US 2015/0045660 A1 Feb. 12, 2015

Related U.S. Application Data

(62) Division of application No. 11/941,819, filed on Nov. 16, 2007, now Pat. No. 8,906,011.

(51) Int. Cl.
*A61B 18/14* (2006.01)
*A61B 5/06* (2006.01)
(Continued)

(52) U.S. Cl.
CPC ............ *A61B 18/1492* (2013.01); *A61B 5/06* (2013.01); *A61B 5/065* (2013.01); *A61B 5/4875* (2013.01);
(Continued)

(58) Field of Classification Search
CPC ......... A61B 5/06; A61B 5/065; A61B 5/4875; A61B 18/1492; A61B 18/18;
(Continued)

(56) References Cited

U.S. PATENT DOCUMENTS 4,114,202 A 9/1978 Roy et al.
4,164,046 A 8/1979 Cooley
(Continued)

FOREIGN PATENT DOCUMENTS

CN 101797181 A 8/2010
EP 0723467 A1 7/1996
(Continued)

OTHER PUBLICATIONS

Buchbinder,Maurice MD, "Dynamic Mitral Valve Annuloplasty: A Reshapable Ring for Residual and Recurring MR," from the Foundation for Cardiovascular Medicine, La Jolla, CA. May 24, 2007.
(Continued)

*Primary Examiner* — Michael Peffley
(74) *Attorney, Agent, or Firm* — Rossi, Kimms & McDowell LLP

(57) ABSTRACT

A device positionable in a cavity of a bodily organ (e.g., a heart) may discriminate between fluid (e.g., blood) and non-fluid tissue (e.g., wall of heart) to provide information or a mapping indicative of a position and/or orientation of the device in the cavity. Discrimination may be based on flow, or some other characteristic, for example electrical permittivity or force. The device may selectively ablate portions of the non-fluid tissue based on the information or mapping. The device may detect characteristics (e.g., electrical potentials) indicative of whether ablation was successful. The device may include a plurality of transducers, intravascularly guided in an unexpanded configuration and positioned proximate the non-fluid tissue in an expanded configuration. Expansion mechanism may include helical member(s) or inflatable member(s).

9 Claims, 16 Drawing Sheets

(51) Int. Cl.
*A61B 5/00* (2006.01)
*A61B 18/18* (2006.01)
*A61B 18/20* (2006.01)
*A61B 18/00* (2006.01)
*A61B 18/02* (2006.01)

(52) U.S. Cl.
CPC .............. *A61B 18/18* (2013.01); *A61B 18/20* (2013.01); *A61B 2018/00214* (2013.01); *A61B 2018/00351* (2013.01); *A61B 2018/00577* (2013.01); *A61B 2018/00702* (2013.01); *A61B 2018/00791* (2013.01); *A61B 2018/025* (2013.01)

(58) Field of Classification Search
CPC   A61B 2018/00577; A61B 2018/00214; A61B 2018/00791; A61B 2018/00702; A61B 2018/025
See application file for complete search history.

(56) References Cited

U.S. PATENT DOCUMENTS

| | | |
|---|---|---|
| 4,225,148 A | 9/1980 | Andersson |
| 4,240,441 A | 12/1980 | Khalil |
| 4,263,680 A | 4/1981 | Reul et al. |
| 4,273,128 A | 6/1981 | Lary |
| 4,411,266 A | 10/1983 | Cosman |
| 4,490,859 A | 1/1985 | Black et al. |
| 4,543,090 A | 9/1985 | McCoy |
| 4,699,147 A | 10/1987 | Chilson et al. |
| 4,770,187 A | 9/1988 | Lash et al. |
| 4,787,369 A | 11/1988 | Allred, III et al. |
| 4,794,912 A | 1/1989 | Lia |
| 4,850,957 A | 7/1989 | Summers |
| 4,887,613 A | 12/1989 | Farr et al. |
| 4,890,602 A | 1/1990 | Hake |
| 4,890,612 A | 1/1990 | Kensey |
| 4,893,613 A | 1/1990 | Hake |
| 4,895,166 A | 1/1990 | Farr et al. |
| 4,905,667 A | 3/1990 | Foerster et al. |
| 4,921,499 A | 5/1990 | Hoffman et al. |
| 4,940,064 A | 7/1990 | Desai |
| 4,942,788 A | 7/1990 | Farr et al. |
| 4,979,514 A | 12/1990 | Sekii et al. |
| 4,998,933 A | 3/1991 | Eggers et al. |
| 5,026,384 A | 6/1991 | Farr et al. |
| 5,047,047 A | 9/1991 | Yoon |
| 5,122,137 A | 6/1992 | Lennox |
| 5,127,902 A | 7/1992 | Fischell |
| 5,156,151 A * | 10/1992 | Imran .................... A61N 1/056 600/375 |
| 5,174,299 A | 12/1992 | Nelson |
| 5,176,693 A | 1/1993 | Pannek, Jr. |
| 5,178,620 A | 1/1993 | Eggers et al. |
| 5,192,291 A | 3/1993 | Pannek, Jr. |
| 5,195,505 A | 3/1993 | Josefsen |
| 5,201,316 A | 4/1993 | Pomeranz et al. |
| 5,228,442 A | 7/1993 | Imran |
| 5,242,386 A | 9/1993 | Holzer |
| 5,245,987 A | 9/1993 | Redmond et al. |
| 5,255,679 A * | 10/1993 | Imran .................. A61B 5/0422 600/375 |
| 5,279,299 A | 1/1994 | Imran |
| 5,293,869 A | 3/1994 | Edwards et al. |
| 5,297,549 A * | 3/1994 | Beatty .................... A61B 5/042 600/374 |
| 5,312,435 A | 5/1994 | Nash et al. |
| 5,317,952 A | 6/1994 | Immega |
| 5,324,284 A | 6/1994 | Imran |
| 5,327,889 A | 7/1994 | Imran |
| 5,341,807 A * | 8/1994 | Nardella ............. A61B 5/0422 600/381 |
| 5,345,936 A | 9/1994 | Pomeranz et al. |
| 5,351,679 A | 10/1994 | Mayzels et al. |
| 5,366,443 A | 11/1994 | Eggers et al. |
| 5,370,679 A | 12/1994 | Atlee, III |
| 5,379,773 A | 1/1995 | Hornsby |
| 5,397,321 A | 3/1995 | Houser et al. |
| 5,419,767 A | 5/1995 | Eggers et al. |
| 5,450,860 A | 9/1995 | O'Connor |
| 5,456,254 A | 10/1995 | Pietroski et al. |
| 5,465,717 A | 11/1995 | Imran et al. |
| 5,478,353 A | 12/1995 | Yoon |
| 5,485,849 A | 1/1996 | Panescu et al. |
| 5,496,267 A | 3/1996 | Drasler et al. |
| 5,499,981 A | 3/1996 | Kordis |
| 5,531,760 A | 7/1996 | Alwafaie |
| 5,545,193 A | 8/1996 | Fleischman et al. |
| 5,549,661 A | 8/1996 | Kordis et al. |
| 5,555,883 A | 9/1996 | Avitall |
| 5,557,967 A | 9/1996 | Renger |
| 5,575,810 A | 11/1996 | Swanson et al. |
| 5,593,424 A | 1/1997 | Northrup, III |
| 5,598,848 A * | 2/1997 | Swanson .............. A61B 5/0422 600/374 |
| 5,599,345 A | 2/1997 | Edwards et al. |
| 5,620,481 A | 4/1997 | Desai et al. |
| 5,637,090 A | 6/1997 | McGee et al. |
| 5,662,587 A | 9/1997 | Grundfest et al. |
| 5,681,308 A | 10/1997 | Edwards et al. |
| 5,681,336 A | 10/1997 | Clement et al. |
| 5,687,723 A | 11/1997 | Avitall |
| 5,687,737 A | 11/1997 | Branham et al. |
| 5,697,285 A | 12/1997 | Nappi et al. |
| 5,713,896 A | 2/1998 | Nardella |
| 5,713,942 A | 2/1998 | Stern et al. |
| 5,716,397 A | 2/1998 | Myers |
| 5,720,726 A | 2/1998 | Marcadis et al. |
| 5,728,114 A | 3/1998 | Evans et al. |
| 5,730,127 A | 3/1998 | Avitall |
| 5,738,096 A * | 4/1998 | Ben-Haim ........... A61B 5/0215 128/899 |
| 5,762,066 A | 6/1998 | Law et al. |
| 5,769,846 A | 6/1998 | Edwards et al. |
| 5,782,239 A | 7/1998 | Webster, Jr. |
| 5,782,879 A | 7/1998 | Rosborough et al. |
| 5,800,495 A | 9/1998 | Machek et al. |
| 5,823,189 A | 10/1998 | Kordis |
| 5,824,066 A | 10/1998 | Gross |
| 5,836,947 A | 11/1998 | Fleischman et al. |
| 5,836,990 A | 11/1998 | Li |
| 5,853,422 A | 12/1998 | Huebsch et al. |
| 5,868,755 A | 2/1999 | Kanner et al. |
| 5,876,343 A | 3/1999 | Teo |
| 5,881,727 A | 3/1999 | Edwards |
| 5,885,278 A | 3/1999 | Fleischman |
| 5,891,136 A | 4/1999 | McGee et al. |
| 5,893,847 A | 4/1999 | Kordis |
| 5,904,711 A | 5/1999 | Flom et al. |
| 5,916,163 A | 6/1999 | Panescu et al. |
| 5,919,207 A | 7/1999 | Taheri |
| 5,921,924 A | 7/1999 | Avitall |
| 5,935,075 A | 8/1999 | Casscells et al. |
| 5,935,079 A | 8/1999 | Swanson et al. |
| 5,941,251 A | 8/1999 | Panescu et al. |
| 5,944,715 A | 8/1999 | Goble et al. |
| 5,961,440 A | 10/1999 | Schweich, Jr. et al. |
| 5,968,040 A | 10/1999 | Swanson et al. |
| 5,984,950 A | 11/1999 | Cragg et al. |
| 6,001,069 A | 12/1999 | Tachibana et al. |
| 6,001,093 A | 12/1999 | Swanson et al. |
| 6,014,581 A | 1/2000 | Whayne et al. |
| 6,023,638 A | 2/2000 | Swanson |
| 6,030,382 A | 2/2000 | Fleischman et al. |
| 6,036,689 A | 3/2000 | Tu et al. |
| 6,063,082 A | 5/2000 | DeVore et al. |
| 6,071,282 A | 6/2000 | Fleischman |
| 6,104,944 A | 8/2000 | Martinelli |
| 6,106,522 A | 8/2000 | Fleischman et al. |
| 6,119,030 A | 9/2000 | Morency |
| 6,123,702 A | 9/2000 | Swanson et al. |
| 6,138,043 A | 10/2000 | Avitall |

(56) References Cited

U.S. PATENT DOCUMENTS

| | | |
|---|---|---|
| 6,142,993 A | 11/2000 | Whayne et al. |
| 6,156,046 A | 12/2000 | Passafaro et al. |
| 6,210,432 B1 | 4/2001 | Solem et al. |
| 6,216,043 B1 | 4/2001 | Swanson et al. |
| 6,217,573 B1 | 4/2001 | Webster |
| 6,241,747 B1 | 6/2001 | Ruff |
| 6,248,124 B1 | 6/2001 | Pedros et al. |
| 6,258,258 B1 | 7/2001 | Sartori et al. |
| 6,266,550 B1 | 7/2001 | Selmon et al. |
| 6,304,769 B1 | 10/2001 | Arenson et al. |
| 6,306,135 B1 | 10/2001 | Ellman et al. |
| 6,308,091 B1 | 10/2001 | Avitall |
| 6,319,249 B1 | 11/2001 | Tollner |
| 6,322,559 B1 | 11/2001 | Daulton et al. |
| 6,330,478 B1 | 12/2001 | Lee et al. |
| 6,346,105 B1 | 2/2002 | Tu et al. |
| 6,350,263 B1 | 2/2002 | Wetzig et al. |
| 6,358,258 B1 | 3/2002 | Arcia et al. |
| 6,383,151 B1 | 5/2002 | Diederich et al. |
| 6,389,311 B1 | 5/2002 | Whayne et al. |
| 6,391,024 B1 | 5/2002 | Sun et al. |
| 6,391,048 B1 | 5/2002 | Ginn et al. |
| 6,391,054 B2 | 5/2002 | Carpentier et al. |
| 6,402,781 B1 | 6/2002 | Langberg et al. |
| 6,436,052 B1 | 8/2002 | Nikolic et al. |
| 6,475,223 B1 | 11/2002 | Werp et al. |
| 6,485,409 B1 | 11/2002 | Voloshin et al. |
| 6,485,482 B1 | 11/2002 | Belef |
| 6,485,489 B2 | 11/2002 | Teirstein et al. |
| 6,506,210 B1 | 1/2003 | Kanner |
| 6,514,249 B1 | 2/2003 | Maguire et al. |
| 6,529,756 B1 | 3/2003 | Phan et al. |
| 6,537,198 B1 | 3/2003 | Vidlund et al. |
| 6,537,314 B2 | 3/2003 | Langberg et al. |
| 6,540,670 B1 | 4/2003 | Hirata et al. |
| 6,551,310 B1 | 4/2003 | Ganz et al. |
| 6,551,312 B2 | 4/2003 | Zhang et al. |
| 6,569,160 B1 | 5/2003 | Goldin et al. |
| 6,569,198 B1 | 5/2003 | Wilson et al. |
| 6,575,971 B2 | 6/2003 | Hauck et al. |
| 6,589,208 B2 | 7/2003 | Ewers et al. |
| 6,616,684 B1 | 9/2003 | Vidlund et al. |
| 6,626,930 B1 | 9/2003 | Allen et al. |
| 6,632,238 B2 | 10/2003 | Ginn et al. |
| 6,635,056 B2 | 10/2003 | Kadhiresan et al. |
| 6,640,119 B1 | 10/2003 | Budd et al. |
| 6,662,034 B2 | 12/2003 | Segner et al. |
| D484,979 S | 1/2004 | Fontaine |
| 6,704,590 B2 | 3/2004 | Haldeman |
| 6,723,038 B1 | 4/2004 | Schroeder et al. |
| 6,726,716 B2 | 4/2004 | Marquez |
| 6,760,616 B2 | 7/2004 | Hoey et al. |
| 6,780,197 B2 | 8/2004 | Roe et al. |
| 6,788,969 B2 | 9/2004 | Dupree et al. |
| 6,797,001 B2 | 9/2004 | Mathis et al. |
| 6,800,090 B2 | 10/2004 | Alferness et al. |
| 6,824,562 B2 | 11/2004 | Mathis et al. |
| 6,837,886 B2 | 1/2005 | Collins et al. |
| 6,852,076 B2 | 2/2005 | Nikolic et al. |
| 6,855,143 B2 | 2/2005 | Davison et al. |
| 6,890,353 B2 | 5/2005 | Cohn et al. |
| 6,892,091 B1 | 5/2005 | Ben-Haim et al. |
| 6,899,674 B2 | 5/2005 | Viebach et al. |
| 6,907,297 B2 | 6/2005 | Wellman et al. |
| 6,908,478 B2 | 6/2005 | Alferness et al. |
| 6,913,576 B2 | 7/2005 | Bowman |
| 6,918,903 B2 | 7/2005 | Bass |
| 6,926,669 B1 | 8/2005 | Stewart et al. |
| 6,942,657 B2 | 9/2005 | Sinofsky et al. |
| 6,949,122 B2 | 9/2005 | Adams et al. |
| 6,960,206 B2 | 11/2005 | Keane |
| 6,960,229 B2 | 11/2005 | Mathis et al. |
| 6,986,775 B2 | 1/2006 | Morales et al. |
| 6,989,010 B2 | 1/2006 | Francischelli et al. |
| 6,989,028 B2 | 1/2006 | Lashinski et al. |
| 6,994,093 B2 | 2/2006 | Murphy et al. |
| 6,997,951 B2 | 2/2006 | Solem et al. |
| 7,001,383 B2 | 2/2006 | Keidar |
| 7,025,776 B1 | 4/2006 | Houser et al. |
| 7,048,734 B1 | 5/2006 | Fleischman et al. |
| 7,050,848 B2 | 5/2006 | Hoey et al. |
| 7,052,487 B2 | 5/2006 | Cohn et al. |
| 7,068,867 B2 | 6/2006 | Adoram et al. |
| 7,141,019 B2 | 11/2006 | Pearlman |
| 7,144,363 B2 | 12/2006 | Pai et al. |
| 7,166,127 B2 | 1/2007 | Spence et al. |
| 7,174,201 B2 | 2/2007 | Govari et al. |
| 7,177,677 B2 | 2/2007 | Kaula et al. |
| 7,186,210 B2 | 3/2007 | Feld et al. |
| 7,187,964 B2 | 3/2007 | Khoury |
| 7,189,202 B2 | 3/2007 | Lau et al. |
| 7,255,695 B2 | 8/2007 | Falwell et al. |
| 7,276,044 B2 | 10/2007 | Ferry et al. |
| 7,279,007 B2 | 10/2007 | Nikolic et al. |
| 7,300,435 B2 | 11/2007 | Wham et al. |
| 7,303,526 B2 | 12/2007 | Sharkey et al. |
| 7,335,196 B2 | 2/2008 | Swanson et al. |
| 7,481,808 B2 | 1/2009 | Koyfman et al. |
| 7,507,252 B2 | 3/2009 | Lashinski et al. |
| 7,530,980 B2 | 5/2009 | Hooven |
| 7,660,452 B2 * | 2/2010 | Zwirn .................. A61B 5/0046 382/131 |
| 7,736,388 B2 | 6/2010 | Goldfarb et al. |
| 7,738,967 B2 | 6/2010 | Salo |
| 8,103,338 B2 | 1/2012 | Harlev et al. |
| D654,588 S | 2/2012 | Taube et al. |
| 8,118,853 B2 | 2/2012 | Grewe |
| 8,150,499 B2 | 4/2012 | Gelbart et al. |
| D660,967 S | 5/2012 | Braido et al. |
| 8,224,432 B2 | 7/2012 | Macadam et al. |
| D717,954 S | 11/2014 | Hjelle et al. |
| 9,198,713 B2 | 12/2015 | Wallace et al. |
| 2001/0003158 A1 | 6/2001 | Kensey et al. |
| 2001/0005787 A1 | 6/2001 | Oz et al. |
| 2001/0018611 A1 | 8/2001 | Solem et al. |
| 2001/0020126 A1 | 9/2001 | Swanson et al. |
| 2001/0021867 A1 | 9/2001 | Kordis et al. |
| 2002/0002329 A1 | 1/2002 | Avitall |
| 2002/0016628 A1 | 2/2002 | Langberg et al. |
| 2002/0087156 A1 | 7/2002 | Maguire et al. |
| 2002/0087173 A1 | 7/2002 | Alferness et al. |
| 2002/0099415 A1 | 7/2002 | Panescu et al. |
| 2002/0107478 A1 | 8/2002 | Wendlandt |
| 2002/0107511 A1 | 8/2002 | Collins et al. |
| 2002/0107530 A1 | 8/2002 | Saucer et al. |
| 2002/0115941 A1 | 8/2002 | Whayne et al. |
| 2002/0115944 A1 | 8/2002 | Mendes et al. |
| 2002/0169504 A1 | 11/2002 | Alferness et al. |
| 2002/0177782 A1 | 11/2002 | Penner |
| 2002/0183836 A1 | 12/2002 | Liddicoat et al. |
| 2002/0183841 A1 | 12/2002 | Cohn et al. |
| 2002/0188170 A1 | 12/2002 | Santamore et al. |
| 2003/0028118 A1 | 2/2003 | Dupree et al. |
| 2003/0028183 A1 | 2/2003 | Sanchez et al. |
| 2003/0050685 A1 | 3/2003 | Nikolic et al. |
| 2003/0055420 A1 | 3/2003 | Kadhiresan et al. |
| 2003/0069570 A1 | 4/2003 | Witzel et al. |
| 2003/0069636 A1 | 4/2003 | Solem et al. |
| 2003/0078465 A1 | 4/2003 | Pai et al. |
| 2003/0078671 A1 | 4/2003 | Lesniak et al. |
| 2003/0105384 A1 | 6/2003 | Sharkey et al. |
| 2003/0105520 A1 | 6/2003 | Alferness et al. |
| 2003/0109770 A1 | 6/2003 | Sharkey et al. |
| 2003/0176810 A1 | 9/2003 | Maahs et al. |
| 2003/0181819 A1 | 9/2003 | Desai |
| 2003/0229395 A1 | 12/2003 | Cox |
| 2004/0002626 A1 | 1/2004 | Feld et al. |
| 2004/0054279 A1 | 3/2004 | Hanley |
| 2004/0133220 A1 | 7/2004 | Lashinski et al. |
| 2004/0133273 A1 | 7/2004 | Cox |
| 2004/0138744 A1 | 7/2004 | Lashinski et al. |
| 2004/0153146 A1 | 8/2004 | Lashinski et al. |
| 2004/0158321 A1 | 8/2004 | Reuter et al. |
| 2004/0176797 A1 | 9/2004 | Opolski |

(56) References Cited

U.S. PATENT DOCUMENTS

| | | |
|---|---|---|
| 2004/0181139 A1 | 9/2004 | Falwell et al. |
| 2004/0186566 A1 | 9/2004 | Hindrichs et al. |
| 2004/0215232 A1 | 10/2004 | Belhe et al. |
| 2004/0243170 A1 | 12/2004 | Suresh et al. |
| 2004/0249408 A1 | 12/2004 | Murphy et al. |
| 2004/0249453 A1 | 12/2004 | Cartledge et al. |
| 2004/0267358 A1 | 12/2004 | Reitan |
| 2005/0004668 A1 | 1/2005 | Aklog et al. |
| 2005/0015109 A1 | 1/2005 | Lichtenstein |
| 2005/0054938 A1 | 3/2005 | Wehman et al. |
| 2005/0055089 A1 | 3/2005 | Macoviak et al. |
| 2005/0060030 A1 | 3/2005 | Lashinski et al. |
| 2005/0064665 A1 | 3/2005 | Han |
| 2005/0065420 A1 | 3/2005 | Collins et al. |
| 2005/0065504 A1 | 3/2005 | Melsky et al. |
| 2005/0080402 A1 | 4/2005 | Santamore et al. |
| 2005/0096047 A1 | 5/2005 | Haberman et al. |
| 2005/0096647 A1 | 5/2005 | Steinke et al. |
| 2005/0107723 A1 | 5/2005 | Wehman et al. |
| 2005/0107871 A1 | 5/2005 | Realyvasquez et al. |
| 2005/0125030 A1 | 6/2005 | Forsberg et al. |
| 2005/0148892 A1 | 7/2005 | Desai |
| 2005/0149014 A1 | 7/2005 | Hauck et al. |
| 2005/0149159 A1 | 7/2005 | Andreas et al. |
| 2005/0154252 A1 | 7/2005 | Sharkey et al. |
| 2005/0182365 A1 | 8/2005 | Hennemann et al. |
| 2005/0187620 A1 | 8/2005 | Pai et al. |
| 2005/0197593 A1 | 9/2005 | Burbank et al. |
| 2005/0197692 A1 | 9/2005 | Pai et al. |
| 2005/0197693 A1 | 9/2005 | Pai et al. |
| 2005/0197694 A1 | 9/2005 | Pai et al. |
| 2005/0203558 A1 | 9/2005 | Maschke |
| 2005/0209636 A1 | 9/2005 | Widomski et al. |
| 2005/0216054 A1 | 9/2005 | Widomski et al. |
| 2005/0240249 A1 | 10/2005 | Tu et al. |
| 2005/0251116 A1 | 11/2005 | Steinke et al. |
| 2005/0251132 A1 | 11/2005 | Oral et al. |
| 2005/0256521 A1 | 11/2005 | Kozel |
| 2005/0261580 A1 | 11/2005 | Willis et al. |
| 2005/0267458 A1 | 12/2005 | Paul et al. |
| 2005/0267574 A1 | 12/2005 | Cohn et al. |
| 2006/0009755 A1 | 1/2006 | Sra |
| 2006/0009756 A1 | 1/2006 | Francischelli et al. |
| 2006/0014998 A1 | 1/2006 | Sharkey et al. |
| 2006/0015002 A1 | 1/2006 | Moaddeb et al. |
| 2006/0015003 A1 | 1/2006 | Moaddes et al. |
| 2006/0015038 A1 | 1/2006 | Weymarn-Scharli |
| 2006/0015096 A1 | 1/2006 | Hauck et al. |
| 2006/0025800 A1 | 2/2006 | Suresh |
| 2006/0030881 A1 | 2/2006 | Sharkey et al. |
| 2006/0085049 A1 | 4/2006 | Cory et al. |
| 2006/0089637 A1 | 4/2006 | Werneth et al. |
| 2006/0100618 A1 | 5/2006 | Chan et al. |
| 2006/0106298 A1 | 5/2006 | Ahmed et al. |
| 2006/0135968 A1 | 6/2006 | Schaller |
| 2006/0135970 A1 | 6/2006 | Schaller |
| 2006/0184242 A1 | 8/2006 | Lichtenstein |
| 2006/0199995 A1 | 9/2006 | Vijay |
| 2006/0229491 A1 | 10/2006 | Sharkey et al. |
| 2006/0235286 A1 | 10/2006 | Stone et al. |
| 2006/0235314 A1 | 10/2006 | Migliuolo et al. |
| 2006/0264980 A1 | 11/2006 | Khairkhahan et al. |
| 2006/0281965 A1 | 12/2006 | Khairkhahan et al. |
| 2006/0293698 A1 | 12/2006 | Douk |
| 2006/0293725 A1 | 12/2006 | Rubinsky et al. |
| 2007/0016068 A1 | 1/2007 | Grunwald et al. |
| 2007/0027533 A1 | 2/2007 | Douk |
| 2007/0038208 A1 | 2/2007 | Kefer |
| 2007/0083193 A1 | 4/2007 | Werneth et al. |
| 2007/0083195 A1 | 4/2007 | Werneth et al. |
| 2007/0088362 A1 | 4/2007 | Bonutti et al. |
| 2007/0115390 A1 | 5/2007 | Makara et al. |
| 2007/0118215 A1 | 5/2007 | Moaddeb |
| 2007/0129717 A1 | 6/2007 | Brown, III et al. |
| 2007/0161846 A1 | 7/2007 | Nikolic et al. |
| 2007/0198058 A1 | 8/2007 | Gelbart et al. |
| 2007/0213578 A1 | 9/2007 | Khairkhahan et al. |
| 2007/0213815 A1 | 9/2007 | Khairkhahan et al. |
| 2007/0232858 A1 | 10/2007 | Macnamara et al. |
| 2007/0249999 A1 | 10/2007 | Sklar et al. |
| 2007/0270688 A1 | 11/2007 | Gelbart et al. |
| 2007/0299343 A1 | 12/2007 | Waters |
| 2008/0004534 A1 | 1/2008 | Gelbart et al. |
| 2008/0004643 A1 | 1/2008 | To et al. |
| 2008/0004697 A1 | 1/2008 | Lichtenstein et al. |
| 2008/0045778 A1 | 2/2008 | Lichtenstein et al. |
| 2008/0071298 A1 | 3/2008 | Khairkhahan et al. |
| 2008/0262337 A1 | 10/2008 | Falwell et al. |
| 2008/0281322 A1 | 11/2008 | Sherman et al. |
| 2008/0312713 A1* | 12/2008 | Wilfley .......... A61B 5/053 607/41 |
| 2009/0018617 A1 | 1/2009 | Skelton et al. |
| 2009/0024138 A1 | 1/2009 | Saleh |
| 2009/0069704 A1 | 3/2009 | MacAdam et al. |
| 2009/0131930 A1 | 5/2009 | Gelbart et al. |
| 2009/0157058 A1 | 6/2009 | Ferren et al. |
| 2009/0171274 A1 | 7/2009 | Harlev et al. |
| 2009/0192441 A1 | 7/2009 | Gelbart et al. |
| 2009/0270737 A1 | 10/2009 | Thornton |
| 2009/0287271 A1 | 11/2009 | Blum et al. |
| 2009/0287304 A1 | 11/2009 | Dahlgren et al. |
| 2010/0121147 A1 | 5/2010 | Oskin et al. |
| 2010/0211052 A1 | 8/2010 | Brown et al. |
| 2010/0249771 A1 | 9/2010 | Pearson et al. |
| 2010/0268059 A1 | 10/2010 | Ryu et al. |
| 2011/0125172 A1 | 5/2011 | Gelbart et al. |
| 2011/0172658 A1 | 7/2011 | Gelbart et al. |
| 2011/0213231 A1 | 9/2011 | Hall et al. |
| 2011/0282491 A1 | 11/2011 | Prisco et al. |
| 2012/0158016 A1 | 6/2012 | Gelbart et al. |
| 2012/0165829 A1 | 6/2012 | Chen et al. |
| 2012/0271135 A1 | 10/2012 | Burke et al. |
| 2013/0165916 A1 | 6/2013 | Mathur et al. |
| 2013/0172883 A1 | 7/2013 | Lopes et al. |
| 2013/0178850 A1 | 7/2013 | Lopes et al. |
| 2013/0178851 A1 | 7/2013 | Lopes et al. |
| 2013/0184705 A1 | 7/2013 | Gelbart et al. |
| 2013/0184706 A1 | 7/2013 | Gelbart et al. |
| 2013/0190587 A1 | 7/2013 | Lopes et al. |
| 2013/0190741 A1 | 7/2013 | Moll et al. |
| 2013/0197513 A1 | 8/2013 | Lopes et al. |
| 2013/0241929 A1 | 9/2013 | Massarwa et al. |
| 2013/0304065 A1 | 11/2013 | Lopes et al. |
| 2013/0310828 A1 | 11/2013 | Reinders et al. |
| 2014/0114307 A1 | 4/2014 | Moisa et al. |
| 2014/0350552 A1 | 11/2014 | Highsmith |
| 2015/0126993 A1 | 5/2015 | Gelbart et al. |
| 2015/0157400 A1 | 6/2015 | Gelbart et al. |

FOREIGN PATENT DOCUMENTS

| | | |
|---|---|---|
| WO | 9510320 A1 | 4/1995 |
| WO | 95/20349 A1 | 8/1995 |
| WO | 97/17892 A1 | 5/1997 |
| WO | 0108575 A2 | 2/2001 |
| WO | 02/087437 A1 | 11/2002 |
| WO | 03015611 A2 | 2/2003 |
| WO | 03077800 A1 | 9/2003 |
| WO | 2004012629 A1 | 2/2004 |
| WO | 2004047679 A1 | 6/2004 |
| WO | 2004084746 A2 | 10/2004 |
| WO | 2004100803 A1 | 11/2004 |
| WO | 2005070330 A1 | 8/2005 |
| WO | 2005102181 A1 | 11/2005 |
| WO | 2006017809 A2 | 2/2006 |
| WO | 2006105121 A2 | 10/2006 |
| WO | 2006135747 A2 | 12/2006 |
| WO | 2006135749 A2 | 12/2006 |
| WO | 2007021647 A2 | 2/2007 |
| WO | 2007115390 A1 | 10/2007 |
| WO | 2008002606 A2 | 1/2008 |
| WO | 2009011721 A1 | 1/2009 |
| WO | 2009065042 A2 | 5/2009 |

(56) References Cited

FOREIGN PATENT DOCUMENTS

| WO | 2012/100184 A2 | 7/2012 |
|---|---|---|
| WO | 2012/100185 A2 | 7/2012 |
| WO | 2013/173917 A1 | 11/2013 |

OTHER PUBLICATIONS

Gabriel et al., "The Dielectric Properties of Biological Tissues: I. Literature Survey," Phys. Med. Biol. 41:2231-2249, 1996.
Konings et al., "Development of an Intravascular Impedance Catheter for Detection of Fatty Lesions in Arteries," IEEE Transactions on Medical Imaging, 16(4):439-446, 1997.
Mack, "New Techniques for Percutaneous Repair of the Mitral Valve," Heart Failure Review, 11:259-268, 2006.
Otasevic et al., "First-in-Man Implantation of Left Ventricular Partitioning Device in a Patient With Chronic Heart Failure: Twelve-Month Follow-up," Journal of Cardiac Failure 13(7):517-520, 2007.
Sharkey et al., "Left Ventricular Apex Occluder. Description of a Ventricular Partitioning Device," EuroIntervention 2:125-127, 2006.
Stiles, et al., "Simulated Characterization of Atherosclerotic Lesions in the Coronary Arteries by Measurement of Bioimpedance," IEE Transactions on Biomedical Engineering, 50(7):916-921,2003.
Tanaka et al., "Artificial SMA Valve for Treatment of Urinary Incontinence: Upgrading of Valve and Introduction of Transcutaneous Transformer," Bio-Medical Materials and Engineering 9:97-112, 1999.
Timek et al.., "Septal-Lateral Annular Cinching ('SLAC') Reduces Mitral Annular Size Without Perturbing Normal Annular Dynamics," Journal of Heart Valve Disease 11 (1):2-10, 2002.
Timek et al., "Septal-Lateral Annular Cinching Abolishes Acute Ischemic Mitral Regurgitation," Journal of Thoracic and Cardiovascular Surgery, 123(5):881-888, 2002.
Valvano et al., "Thermal Conductivity and Diffusivity of Biomaterials Measured with Self-Heated Thermistors," International Journal of Thermodynamics, 6(3):301-311, 1985.
Gelbart et al., "Automatic Atherectomy System," Office Action mailed Mar. 4, 2009 for U.S. Appl. No. 11/436,584, 7 pages.
Gelbart et al., "Automatic Atherectomy System," Amendment filed Aug. 4, 2009 for U.S. Appl. No. 11/436,584, 35 pages.
Gelbart et al., "Automatic Atherectomy System," Office Action mailed Dec. 1, 2009 for U.S. Appl. No. 11/436,584, 10 pages.
Gelbart et al., "Automatic Atherectomy System," Amendment filed Mar. 30, 2010 for U.S. Appl. No. 11/436,584, 20 pages.
Gelbart et al., "Automatic Atherectomy System," Amendment filed Oct. 25, 2010 for U.S. Appl. No. 11/436,584, 9 pages.
Gelbart et al., "Automatic Atherectomy System," Office Action mailed Dec. 14, 2010 for U.S. Appl. No. 11/436,584, 12 pages.
Gelbart et al., "Intra-Cardiac Mapping and Ablation Method," Preliminary Amendment filed Aug. 29, 2007 for U.S. Appl. No. 11/475,950,42 pages.
Gelbart et al., "Intra-Cardiac Mapping and Ablation Method," Amendment filed Mar. 5, 2008 for U.S. Appl. No. 11/475,950, 11 pages.
Gelbart et al., "Intra-Cardiac Mapping and Ablation Method," Office Action mailed Jun. 23, 2010 for U.S. Appl. No. 11/475,950, 18 pages.
Gelbart et al., "Intra-Cardiac Mapping and Ablation Method," Amendment filed Aug. 16, 2010 for U.S. Appl. No. 11/475,950,22 pages.
Gelbart et al., "Intra-Cardiac Mapping and Ablation Method," Office Action mailed Nov. 23, 2010 for U.S. Appl. No. 11/475,950,25 pages.
Gelbart et al., "Intra-Cardiac Mapping and Ablation Method," Amendment filed Feb. 23, 2011 for U.S. Appl. No. 11/475,950, 28 pages.
Gelbart et al., "Automatic Atherectomy System," Office Action mailed Jun. 15, 2011, for U.S. Appl. No. 12/950,871, 16 pages.
Gelbart et al., "Liposuction System," Office Action mailed Mar. 16, 2011 for U.S. Appl. No. 12/010,458, 12 pages.
Gelbart et al., "Liposuction System," Amendment filed Jun. 10, 2011 for U.S. Appl. No. 12/010,458, 10 pages.
Lichtenstein "Method and Apparatus for Percutaneous Reduction of Anterior-Posterior Diameter of Mitral Valve," U.S. Appl. No. 10/690,131, filed Oct. 20, 2003, 31 pages.
International Search Report, mailed Dec. 5, 2007, for PCT/US2007/014902, 5 pages.
International Preliminary Report on Patentability, issued Jan. 6, 2009, for PCT/US2007/014902, 8 pages.
International Search Report, mailed Dec. 2, 2009, for PCT/US2008/083644, 5 pages.
Written Opinion, mailed Dec. 5, 2007, for PCT/US2007/014902, 7 pages.
Written Opinion, mailed Dec. 2, 2009, for PCT/US2008/083644, 9 pages.
Gelbart et al., "Automatic Atherectomy System," Amendment filed Sep. 15, 2011 for U.S. Appl. No. 12/950,871, 21 pages.
Gelbart et al., "Liposuction System," Amendment filed Dec. 7, 2011 for U.S. Appl. No. 12/010,458, 15 pages.
Gelbart et al., "Liposuction System," Office Action mailed Sep. 14, 2011 for U.S. Appl. No. 12/010,458, 9 pages.
Gelbart et al, "Apparatus and Method for Intra-Cardiac Mapping and Ablation", Notice of Allowance dated Oct. 23, 2014 for U.S. Appl. No. 11/475,950, 10 pgs.
Gelbart et al., "Medical Device for Use in Bodily Lumens, for Example an Atrium", Notice of Allowance mailed Nov. 13, 2014 for U.S. Appl. No. 13/070,215, 54 pages.
Official Action issued in CN201280004400.9, mailed Dec. 3, 2014.
International Search Report mailed Mar. 10, 2015, for International Application PCT/CA2014/051144; 10 pages.
Written Opinion mailed Mar. 10, 2015, for International Application PCT/CA2014/051144; 4 pages.
Biotronik's "AlCath Flutter Gold Cath for Atrial Flutter Available in EU", Sep. 19, 2013, medGadget, 3 pgs, http://www.medgadget.com/2013/09/biotroniks-alcath-flutter-gold-cath-for-atrial-flutter-unveiled-in-europe.html [Jun. 24, 2014 2:37:09 PM].
Non-final Office Action issued in co-pending U.S. Appl. No. 13/782,867, dated Apr. 15, 2015.
Non-final Office Action issued in co-pending U.S. Appl. No. 13/782,903, dated Apr. 28, 2015.
Lopes et al., "Enhanced Medical Device for Use in Bodily Cavities, for Example an Atrium", Office Action mailed May 22, 2015 for U.S. Appl. No. 13/782,889, 86 pages.
Lopes et al., "High-Density Electrode-Based Medical Device System", Office Action mailed Jul. 10, 2015 for U.S. Appl. No. 13/793,076, 98 pages.
Lopes et al., "High-Density Electrode-Based Medical Device System", Office Action mailed Jul. 9, 2015 for U.S. Appl. No. 13/793,213, 99 pages.
Gelbart et al., "Apparatus and Method for Intra-Cardiac Mapping and Ablation", Office Action mailed Aug. 5, 2015 for U.S. Appl. No. 13/785,910, 79 pages.
Lopes et al., "Enhanced Medical Device for Use in Bodily Cavities, for Example an Atrium", Amendment filed Aug. 24, 2015 for U.S. Appl. No. 13/782,889, 21 pages.
Lopes et al., "Enhanced Medical Device for Use in Bodily Cavities, for Example an Atrium", Amendment filed Aug. 28, 2015 for U.S. Appl. No. 13/782,903, 19 pages.
Lopes et al., "Enhanced Medical Device for Use in Bodily Cavities, for Example an Atrium", Amendment filed Sep. 14, 2015 for U.S. Appl. No. 13/782,867, 25 pages.
Lopes et al., "High-Density Electrode-Based Medical Device System", Amendment filed Oct. 9, 2015 for U.S. Appl. No. 13/793,213, 26 pages.
Lopes et al., "High-Density Electrode-Based Medical Device System", Amendment filed Oct. 9, 2015 for U.S. Appl. No. 13/793,076, 14 pages.
Examination Report issued in EP13172848.7, mailed Sep. 21, 2015.
Extended European Search Report issued in EP13793216.6, mailed Oct. 30, 2015.

(56) References Cited

OTHER PUBLICATIONS

Moisa et al., "Catheter System", Office Action mailed Nov. 16, 2015 for U.S. Appl. No. 14/136,946, 92 pages.
Office Action issued in U.S. Appl. No. 13/782,889, mailed Dec. 18, 2015.
Office Action issued in U.S. Appl. No. 13/782,903, mailed Dec. 18, 2015.
Extended European Search Report issued in EP15188407.9, mailed Jan. 21, 2016.
Lopes et al. "Enhanced Medical Device for Use in Bodily Cavities, for Example an Atrium", Office Action mailed Jan. 25, 2016 for U.S. Appl. No. 13/782,867, 49 pages.
Notice of Allowance issued in U.S. Appl. No. 13/793,076, dated Feb. 10, 2016.
Final Office Action issued in U.S. Appl. No. 13/793,213, dated Feb. 26, 2016.
Non-Final Office Action issued in U.S. Appl. No. 29/509,719, dated Feb. 25, 2016.
Quayle issued in U.S. Appl. No. 29/509,621, dated Feb. 26, 2016.
Quayle issued in U.S. Appl. No. 29/509,636, dated Feb. 26, 2016.
Non-Final Office Action issued in U.S. Appl. No. 13/785,910 mailed Apr. 8, 2016.
Non-Final Office Action issued in U.S. Appl. No. 14/229,250 mailed Apr. 28, 2016.
Non-Final Office Action issued in U.S. Appl. No. 14/229,305 mailed Apr. 29, 2016.
Notice of Allowance issued in U.S. Appl. No. 13/793,076 mailed Jul. 7, 2016.
Notice of Allowance issued in U.S. Appl. No. 13/793,213 mailed Aug. 10, 2016.
Non-Final Office Action issued in U.S. Appl. No. 13/942,354 mailed Aug. 4, 2016.
Notice of Allowance issued in U.S. Appl. No. 14/136,946 mailed May 12, 2016.
Notice of Allowance issued in U.S. Appl. No. 13/782,867 mailed Aug. 12, 2016.
Notice of Allowance issued in U.S. Appl. No. 13/782,903 mailed Jul. 6, 2016.
Corrected Notice of Allowance issued in U.S. Appl. No. 13/782,903 mailed Jul. 19, 2016.
Notice of Allowance issued in U.S. Appl. No. 13/782,889, mailed Aug. 25, 2016.
Notice of Allowance issued in U.S. Appl. No. 29/509,636, mailed Sep. 27, 2016.
Notice of Allowance issued in U.S. Appl. No. 29/509,621, mailed Sep. 27, 2016.
Office Action issued in U.S. Appl. No. 13/785,910, mailed Nov. 2, 2016.
Notice of Allowance issued in U.S. Appl. No. 14/229,305, mailed Nov. 8, 2016.
Notice of Allowance issued in U.S. Appl. No. 14/229,250, mailed Dec. 7, 2016.
Becker R. et al, "Ablation of Atrial Fibrillation: Energy Sources and Navigation Tools: A Review", Journal of Electrocardiology, 37 (Supplement 2004): 55-62, 2004.
Calkins, Hugh, "Radiofrequency Catheter Ablation of Supraventricular Arrhythmias", Heart, 85:594-600, 2001.
De Ponti et al., "Non-Fluoroscopic Mapping Systems for Electrophysiology: The 'Tool or Toy' Dilemma After 10 Years",European Heart Journal 27:1134-1136, 2006.
Gelbart et al, "Apparatus and Method for Intra-Cardiac Mapping and Ablation", Office Action dated Dec. 13, 2013; Notice of Allowance dated Jul. 25, 2014 for co-pending U.S. Appl. No. 11/475,950, 19 pgs.
Gelbart et al., "Medical Device for Use in Bodily Lumens, for Example an Atrium", Office Action dated Jan. 3, 2012; Office Action dated Apr. 3, 2014; Notice of Allowance dated Aug. 26, 2014 for co-pending U.S. Appl. No. 11/941,819, 35 pgs.
Gelbart et al, "Apparatus and Method for Intra-Cardiac Mapping and Ablation", Amendment filed Apr. 10, 2014; Supplemental Amendment filed Feb. 12, 2013 for co-pending U.S. Appl. No. 11/475,950, 21 pgs.
Gelbart et al, "Apparatus and Method for Intra-Cardiac Mapping and Ablation", Preliminary Amendment filed Aug. 22, 2014; Preliminary Amendment filed Mar. 5, 2013 for co-pending U.S. Appl. No. 13/785,910, 10 pgs.
Gelbart et al, "Apparatus and Method for Intra-Cardiac Mapping and Ablation", Preliminary Amendment filed Aug. 22, 2014; Preliminary Amendment filed Mar. 5, 2013 for co-pending U.S. Appl. No. 13/785,931, 10 pgs.
Lopes et al, "Enhanced Medical Device for Use in Bodily Cavities, for Example an Atrium", Preliminary Amendment filed Oct. 22, 2013 for co-pending U.S. Appl. No. 13/942,354, 13 pgs.
Lopes et al, "Enhanced Medical Device for Use in Bodily Cavities, for Example an Atrium", Preliminary Amendment filed Aug. 20, 2014 for co-pending U.S. Appl. No. 13/782,889, 11 pgs.
Lopes et al, "Enhanced Medical Device for Use in Bodily Cavities, for Example an Atrium", Preliminary Amendment filed Mar. 14, 2013 for co-pending U.S. Appl. No. 13/782,867, 8 pgs.
Gelbart et al., "Medical Device for Use in Bodily Lumens, for Example an Atrium", Amendment filed Jul. 3, 2014; Amendment filed Apr. 2, 2012; Amendment filed Mar. 1, 2012; Amendment filed Nov. 23, 2011; Replacement drawings filed Feb. 13, 2008 for U.S. Appl. No. 11/941,819, 155 pgs.
Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,305, 12 pgs.
Gelbart et al., "Medical Device for Use in Bodily Lumens, for Example an Atrium", Preliminary Amendment filed May 12, 2014; Preliminary Amendment filed May 2, 2014 for U.S. Appl. No. 14/229,250, 10 pgs.
Gelbart et al., Medical Device for Use in Bodily Lumens, for Example an Atrium, Amendment filed Sep. 22, 2014, for co-pending U.S. Appl. No. 13/070,215, 18 pgs.
Gelbart et al., Medical Device for Use in Bodily Lumens, for Example an Atrium, Office Action dated Jun. 20, 2014, for co-pending U.S. Appl. No. 13/070,215, 8 pgs.
Gelbart et al., "Medical Device for Use in Bodily Lumens, for Example an Atrium", Supplemental Notice of Allowance dated Oct. 6, 2014 for co-pending U.S. Appl. No. 11/941,819, 4 pgs.
Bard, "Mesh Ablator Catheter", Brochure, 2008, 4 pgs, Bard Electrophysiology Division, C.R. Bard Inc., 55 Technology Drive Lowell, MA 07851 USA.
Biotronik's "AlCath Flutter Gold Cath for Atrial Flutter Available in EU", medGadget, 3 pgs, http://www.medgadget.com/2013/09/biotroniks-alcath-flutter-gold-cath-for-atrial-flutter-unveiled-in-europe.html[Jun. 24, 2014 2:37:09 PM].
"Constellation Mapping Catheters", Brochure, Boston Scientific Corp., 2 pgs © 2007 Boston Scientific Corporation.
"Waveforms and Segments", Ensite System Instructions for use, 54-06154-001 Rev02, Chapter 7 pp. 85-90 © 2007 St. Jude Medical.
Extended European Search Report and EP search opinion for corresponding EP 12736677.1, mail date Mar. 28, 2014.
Extended European Search Report and EP search opinion for corresponding EP 12736962.7, mail date Mar. 28, 2014.
Extended European Search Report mailed Aug. 20, 2013 issued in EP Patent Application No. 13172848.7.
Written Opinion dated Aug. 22, 2012 for PCT/US2012/022061, 6 pgs.
International Search Report and Written Opinion mailed Aug. 2, 2013 issued in PCT/CA2013/050350.
International Search Report and Written Opinion mailed Sep. 17, 2013 issued in PCT/US2013/039982.
International Search Report and Written Opinion mailed Sep. 27, 2013 issued in PCT/US2013/039977.
International Search Report dated Jul. 30, 2012 for PCT/US2012/022062, 5 pgs.
Written Opinion dated Jul. 30, 2012 for PCT/US2012/022062, 5 pgs.

(56) References Cited

OTHER PUBLICATIONS

International Search Report dated Aug. 22, 2012 for PCT/US2012/022061, 5 pgs.
"Phased RF Catheter Ablation System", 2014 Medtronic Inc., 2 pgs, http://www.medtronic.eu/your-health/atrial-fibrillation/about-the-therapy/our-phased-rf-ablation-system/[Jun. 24, 2014 2:38:05 PM].
"ThermoCool® Irrigated Tip Catheter", Brochure, Biosense Webster, 4 pgs , Biosense Webster, Inc. 3333 Diamond Canyon Road Diamond Bar, CA 91765, USA, © Biosense Webster, Inc. 2009 All rights reserved. 1109003.0.
NPL Gelbart "Medical Device for Use in Bodily Lumens, for Example an Atrium", OA mailed Jul. 25, 2011 for U.S. Appl. No. 11/941,819, now published as US 2009-0131930 A1.
Lopes et al., "High-Density Electrode-Based Medical Device System", Amendment filed in co-pending U.S. Appl. No. 13/793,076 on May 9, 2016, 15 pgs.
Lopes et al., "High-Density Electrode-Based Medical Device System", Preliminary Amendment filed in co-pending U.S. Appl. No. 13/793,076 on May 26, 2016, 15 pgs.
Lopes et al., "High-Density Electrode-Based Medical Device System" Amendment filed in co-pending U.S. Appl. No. 13/793,213 on May 26, 2016, 39 pgs.
Lopes et al., "High-Density Electrode-Based Medical Device System", Preliminary Amendment filed in co-pending U.S. Appl. No. 15/287,988 on Nov. 23, 2016, 9 pgs.
Gelbart et al., "Intra-Cardiac Mapping and Ablation Method", Amendment filed in co-pending U.S. Appl. No. 11/475,950 on Feb. 12, 2013, 4 pgs.
Gelbart et al., "Apparatus and Method for Intra-Cardiac Mapping and Ablation", Amendment filed in co-pending U.S. Appl. No. 13/785,910 on Jan. 5, 2016, 15 pgs.
Gelbart et al., "Apparatus and Method for Intra-Cardiac Mapping and Ablation", Amendment filed in co-pending U.S. Appl. No. 13/785,910 on Feb. 9, 2016, 11 pgs.
Gelbart et al., "Apparatus and Method for Intra-Cardiac Mapping and Ablation", Amendment filed in co-pending U.S. Appl. No. 13/785,910 on Aug. 8, 2016, 18 pgs.
Gelbart et al., "Apparatus and Method for Intracardiac Mapping and Ablation", Preliminary Amendment filed in co-pending U.S. Appl. No. 13/785,931 on Mar. 5, 2013, 2 pgs.
Gelbart et al., "Apparatus and Method for Intra-Cardiac Mapping and Ablation", Preliminary Amendment filed in co-pending U.S. Appl. No. 14/804,924 on Jul. 30, 2015, 5 pgs.
Lopes et al., "Enhanced Medical Device for Use in Bodily Cavities, for Example an Atrium", Amendment filed in co-pending U.S. Appl. No. 13/942,354 on Jan. 4, 2017, 23 pgs.
Moisa et al., "Catheter System", Amendment filed in co-pending U.S. Appl. No. 14/136,946 on Apr. 18, 2016, 19 pgs.
Moisa et al., "Catheter System", Preliminary Amendment filed in co-pending U.S. Appl. No. 15/254,130 on Sep. 19, 2016, 22 pgs.
Lopes et al., "Enhanced Medical Device for Use in Bodily Cavities, for Example an Atrium", Amendment filed in co-pending U.S. Appl. No. 13/782,889 on May 17, 2016, 51 pgs.
Lopes et al., "Enhanced Medical Device for Use in Bodily Cavities, for Example an Atrium", Amendment filed in co-pending U.S. Appl. No. 13/782,867 on May 17, 2016, 39 pgs.
Lopes et al., "Enhanced Medical Device for Use in Bodily Cavities, for Example an Atrium", Preliminary Amendment filed in co-pending U.S. Appl. No. 15/299,640 on Oct. 21, 2016, 4 pgs.
Lopes et al., "Enhanced Medical Device for Use in Bodily Cavities, for Example an Atrium", Preliminary Amendment filed in co-pending U.S. Appl. No. 15/299,640 on Dec. 9, 2016, 11 pgs.
Gelbart et al., "Medical Device for Use in Bodily Lumens, for Example an Atrium", Preliminary Amendment filed in co-pending U.S. Appl. No. 14/713,114 on Jun. 16, 2015, 8 pgs.
Gelbart et al., "Medical Device for Use in Bodily Lumens, for Example an Atrium", Preliminary Amendment filed in co-pending U.S. Appl. No. 14/713,190 on May 15, 2015, 3 pgs.
Gelbart et al., "Medical Device for Use in Bodily Lumens, for Example an Atrium", Preliminary Amendment filed in co-pending U.S. Appl. No. 14/713,190 on Jun. 16, 2015, 7 pgs.
Gelbart et al., "Medical Device for Use in Bodily Lumens, for Example an Atrium", Amendment filed in co-pending U.S. Appl. No. 14/229,305 on Sep. 27, 2016, 15 pgs.
Gelbart et al., "Medical Device for Use in Bodily Lumens, for Example an Atrium", Amendment filed in co-pending U.S. Appl. No. 14/229,250 on Sep. 27, 2016, 13 pgs.
Lopes et al., "Intra-Cardiac Procedure Device", Amendment filed in co-pending U.S. Appl. No. 29/509,621 on Nov. 17, 2016, 3 pgs.
Lopes et al., "Intra-Cardiac Procedure Device", Amendment filed in co-pending U.S. Appl. No. 29/509,621 on Jul. 22, 2016, 5 pgs.
Lopes et al., "Intra-Cardiac Procedure Device", Amendment filed in co-pending U.S. Appl. No. 29/509,636, filed Jul. 22, 2016, 5 pgs.
Lopes et al., "Intra-Cardiac Procedure Device", Amendment filed in co-pending U.S. Appl. No. 29/509,636 on Nov. 17, 2016, 3 pgs.
Notice of Allowance issued in U.S. Appl. No. 13/942,354 mailed Feb. 10, 2017.
Office Action issued in U.S. Appl. No. 14/564,463 mailed Feb. 28, 2017.
Decision to Refuse a European Patent Application issued in European Patent Application No. 13172848.7 mailed Feb. 22, 2017.
Gelbart et al., "Apparatus and Method for Intra-Cardiac Mapping and Ablation", Amendment filed in co-pending U.S. Appl. No. 13/785,910 on Mar. 24, 2017, 30 pgs.
Office Action issued in Chinese Patent Application No. 201510432392.3 mailed Mar. 8, 2017. English concise Explanation of Relevance provided.
Gelbart et al., "Apparatus and Method for Intra-Cardiac Mapping and Ablation", Preliminary Amendment filed in co-pending U.S. Appl. No. 14/804,810 on Jul. 30, 2015, 10 pgs.

* cited by examiner

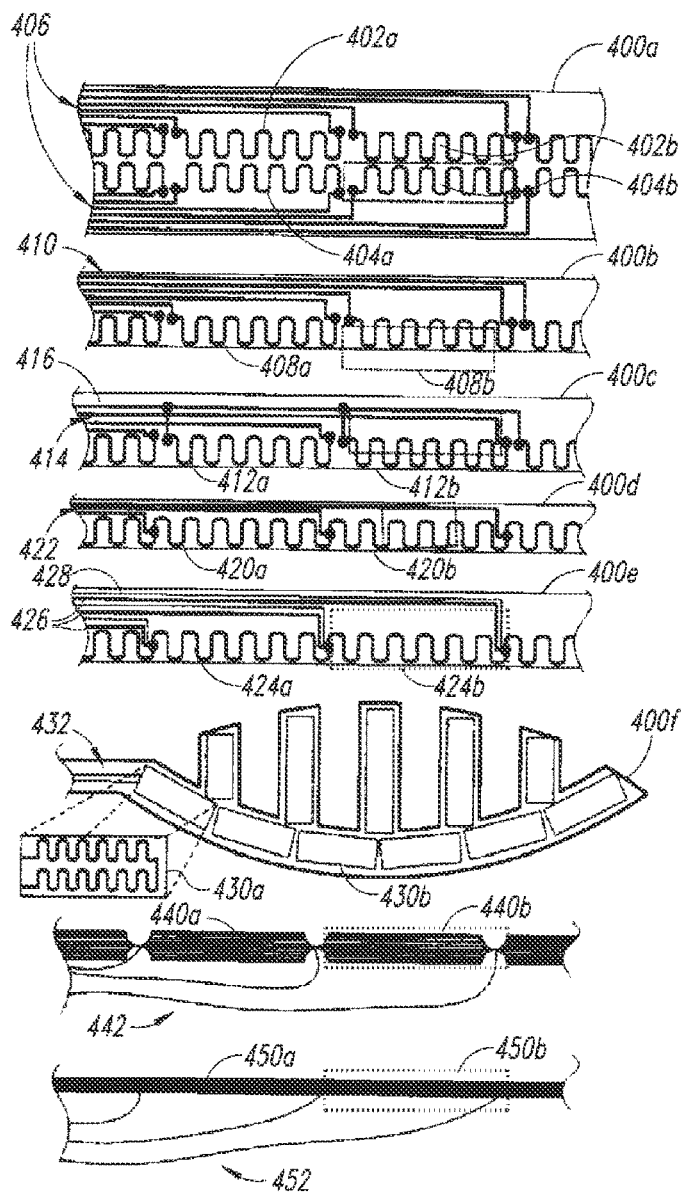
FIG. 4A
FIG. 4B
FIG. 4C
FIG. 4D
FIG. 4E
FIG. 4F
FIG. 4G
FIG. 4H
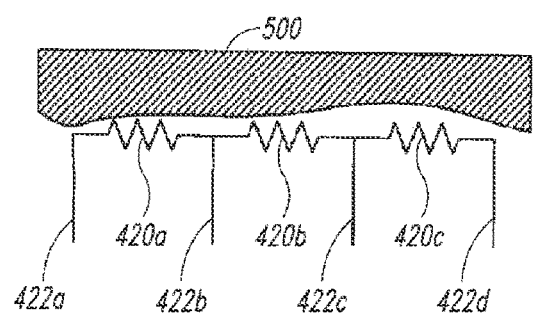
FIG. 5

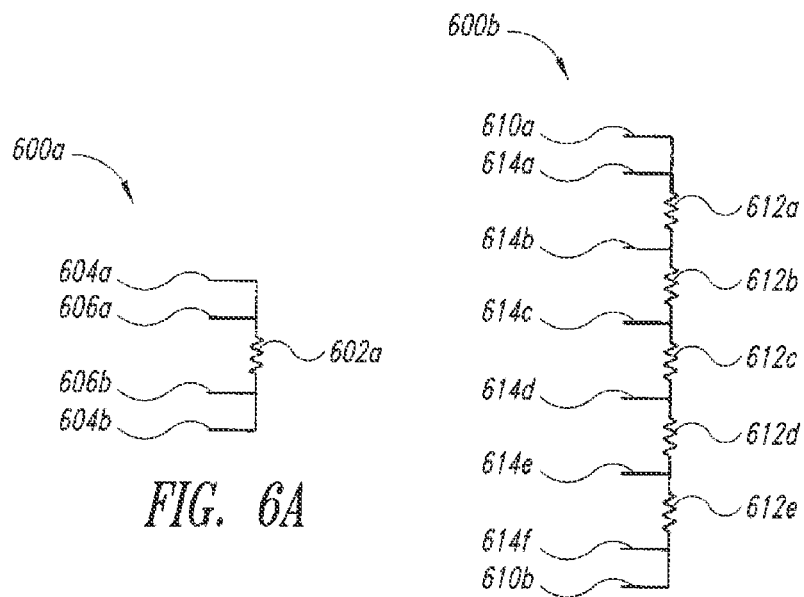
FIG. 6A
FIG. 6B
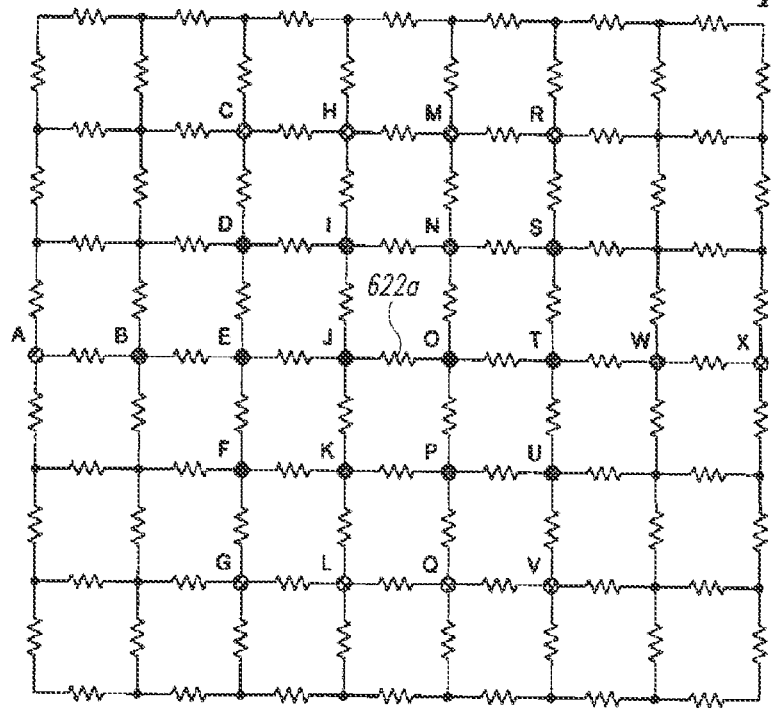
FIG. 6C

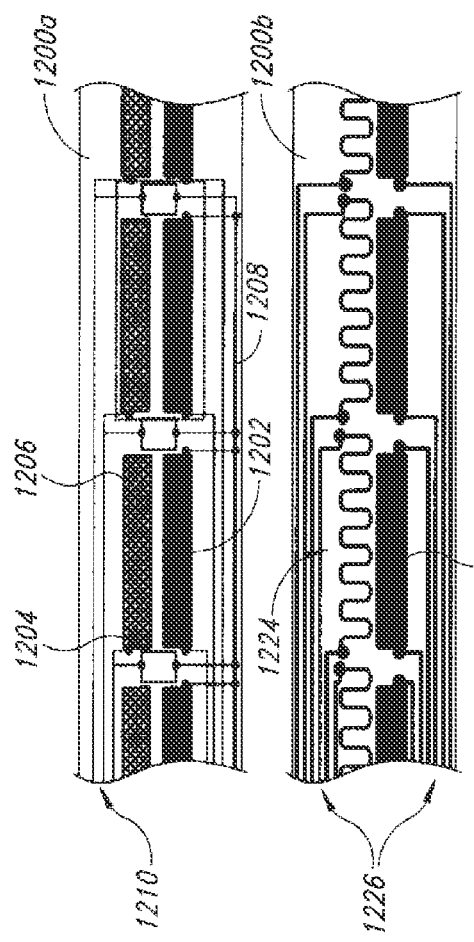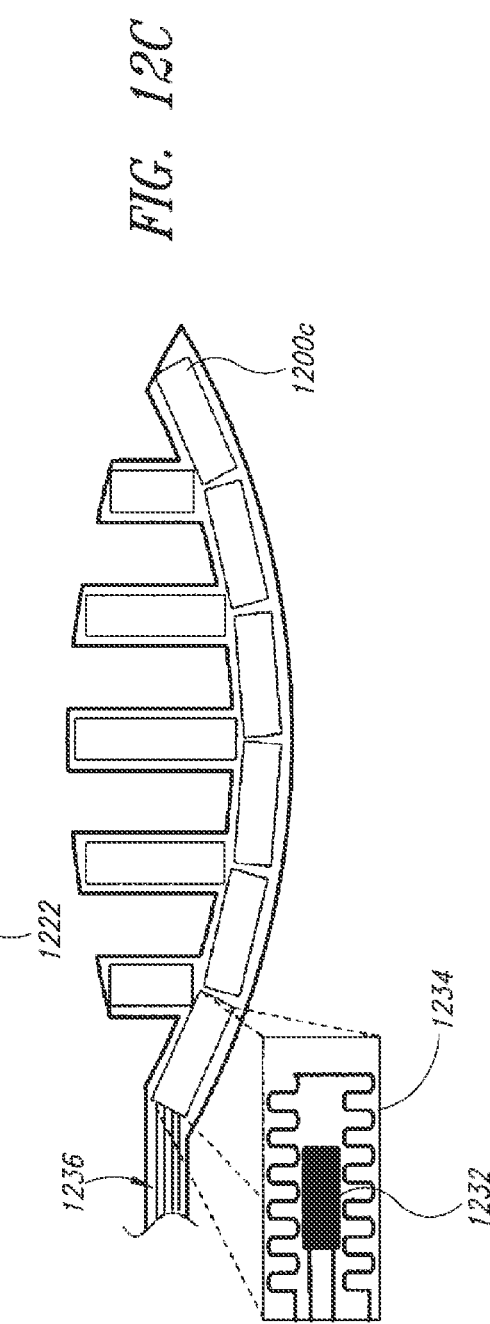
FIG. 12A
FIG. 12B
FIG. 12C

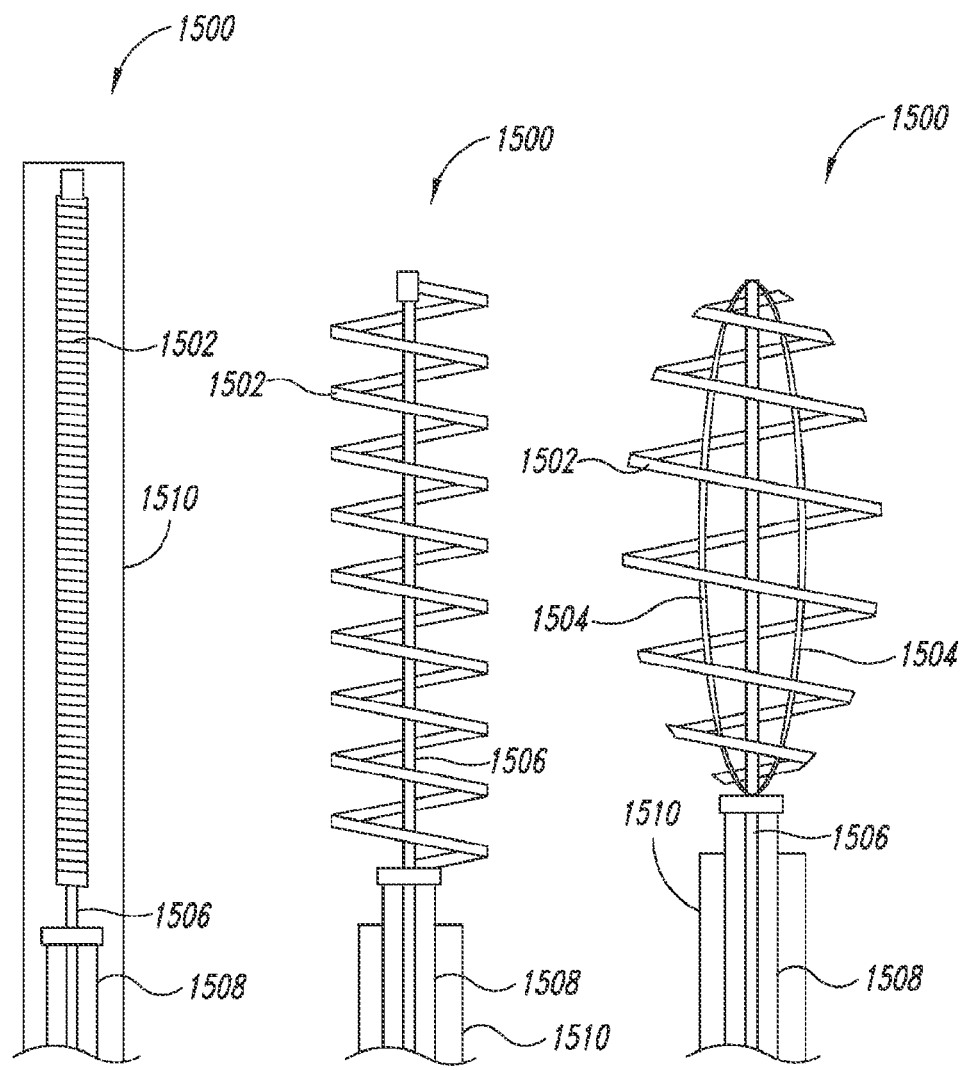
*FIG. 15A*  *FIG. 15B*  *FIG. 15C*

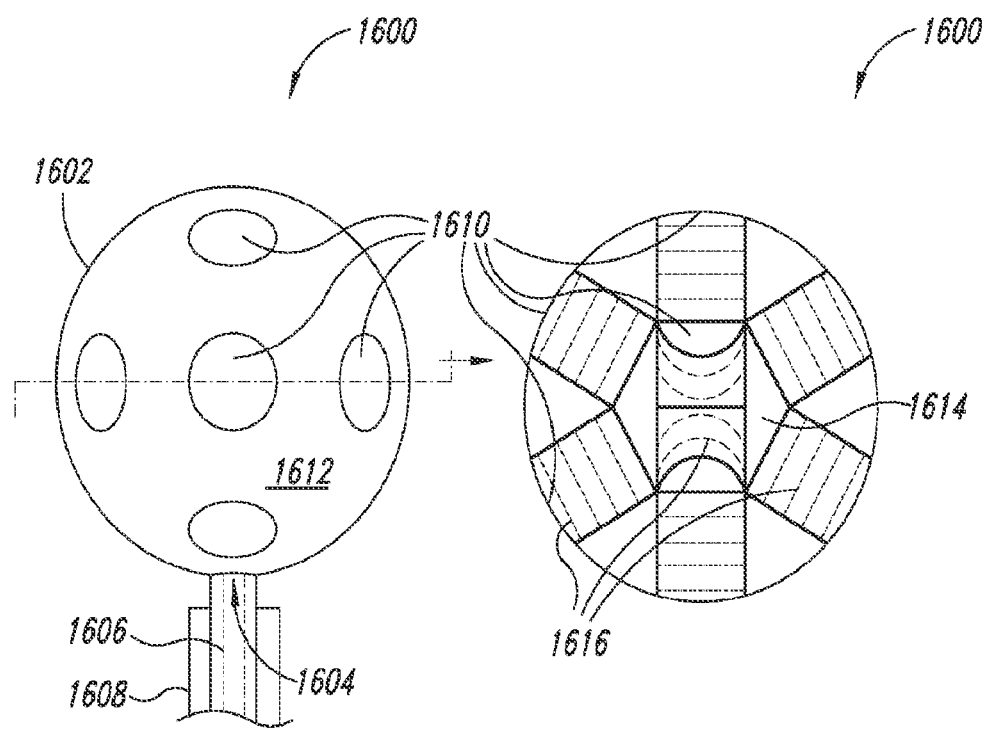
*FIG. 16A*  *FIG. 16B*

MEDICAL DEVICE FOR USE IN BODILY LUMENS, FOR EXAMPLE AN ATRIUM

CROSS-REFERENCE TO RELATED APPLICATION

This application is a divisional of and claims benefit to U.S. patent application Ser. No. 11/941,819, filed Nov. 16, 2007, now U.S. Pat. No. 8,906,011, issued Dec. 9, 2014, the content of which is hereby incorporated herein by reference.

BACKGROUND

Field

This disclosure is generally related to percutaneous cardiac surgery, and more particularly to percutaneously deployed medical devices suitable for determining locations of cardiac features and/or ablating regions of cardiac tissue.

Description of the Related Art

Cardiac surgery was initially undertaken only by performing a sternotomy, a type of incision in the center of the chest, that separates the sternum (chestbone) to allow access to the heart. In the previous several decades, more and more cardiac operations are performed using percutaneous techniques, that is medical procedures where access to inner organs or other tissue is gained via a catheter.

Percutaneous surgeries benefit patients by reducing surgery risk, complications and recovery time. However, the use of percutaneous technologies also raises some particular challenges. Medical devices used in percutaneous surgery need to be deployed via narrow tubes called catheter sheaths, which significantly increase the complexity of the device structure. As well, doctors do not have direct visual contact with the medical tools used once they are placed within the body, and positioning the tools correctly and operating the tools successfully can often be very challenging.

One example of where percutaneous medical techniques are starting to be used is in the treatment of a heart disorder called atrial fibrillation. Atrial fibrillation is a disorder in which spurious electrical signals cause an irregular heart beat. Atrial fibrillation has been treated successfully in open heart methods using a technique know as the "Maze procedure". During this procedure, doctors create lesions in a specific pattern in the left and right atriums that eliminate the spurious electrical signals. Such lesions were originally created using incisions, but are now typically created by ablating the tissue with RF energy. The procedure is performed with a high success rate under direct vision, but is relatively complex to perform percutaneously because of the difficulty in creating the lesions in the correct spots. Substantial problems, potentially leading to severe adverse results, may occur if the lesions are placed incorrectly.

Key factors which are needed to dramatically improve the percutaneous treatment of atrial fibrillation are enhanced methods for deployment, positioning, and operation of the treatment device. It is particularly important to know the position of the elements which will be creating the lesions relative to cardiac features such as the pulmonary veins and mitral valve.

Several methods have been previously developed for positioning percutaneously deployed medical devices with the heart. However, there are significant challenges associated with each of these methods. One method is to map the inside of the atrium by sensing electrical activity on the atrium wall. Devices that use such a method require intimate electrical contact with the atrium wall which is not always possible because of scar tissue and deposits. Also, such devices fail to accurately map the edges of the openings where the veins enter the atrium, which is important for correct placement of the ablation pattern. Other methods, such as using an array of ultrasonic transducers, are not practical as devices that make use of such methods will not fit through a catheter of a reasonable size (6-8 mm diameter). Yet another method for positioning the treatment device is to make use of an external system for providing navigation, such as a magnetic positioning system. These systems are very expensive and have difficulty delivering the resolution and accuracy needed for correct placement of ablation.

Atrial fibrillation is but one example of a cardiac surgery that requires improved navigation and deployment for percutaneous treatment. There are many others that require similar improvement, such as mitral valve repair.

Thus, there is a need for methods and apparatus that improve navigation and percutaneous deployment of medical devices, as well as determination of the relative position of cardiac features such as pulmonary veins and the mitral valve with respect to a medical device. There is a further need for methods and apparatus that allow the formation of lesions in a specified position relative to cardiac features such as pulmonary veins and the mitral valve.

BRIEF SUMMARY OF THE INVENTION

The present design of a medical device with enhanced capabilities for deployment, positioning and ablating within the heart employs a method for distinguishing tissue from blood and may be used to deliver superior positional information of the device relative to ports in the atrium, such as the pulmonary veins and mitral valve. The device may employ methods such as blood flow detection, impedance change detection or deflection force detection to discriminate between blood and tissue. The device may also improve ablation positioning and performance by using the same elements for discriminating between blood and tissue as are used for ablation. Other advantages will become apparent from the teaching herein to those of skill in the art.

At least one embodiment may be summarized as a method of operating a medical system including sensing at least one characteristic by each of a number of transducer elements carried by a device located in at least a portion of a bodily organ, the at least one characteristic indicative of at least one of a presence of a fluid (e.g., blood) and a presence of non-fluid tissue (e.g., wall of heart); computationally discriminating between the fluid and the non-fluid tissue based at least in part on the at least one characteristic sensed by at least some of the transducer elements; and providing information indicative of at least a position of the device in the bodily organ based on the computational discrimination between the fluid and the non-fluid tissue.

The method may further include ablating a portion of the non-fluid tissue in a bodily organ, for example the heart. The method may further include sensing an electrical potential of the non-blood tissue in the heart at least once after the ablating; and producing an indication based on the sensed electrical potential of the non-blood tissue indicative of whether the ablating was successful. Sensing at least one characteristic by each of a number of transducer elements may include sensing a permittivity of the fluid or the non-fluid tissue at each of a plurality of frequencies. Sensing at least one characteristic by each of a number of transducer elements may include sensing a force exerted on the sensor by the fluid or non-fluid tissue. Providing information indicative of at least a position of the device in the bodily organ based on the computational discrimination between the fluid and the non-fluid tissue may include providing information indicative of a three-dimensional pose of the device with respect to at least the portion of a heart. The method may further include intravascularly guiding the device to a desired position while at least a portion of the device is in an unexpanded configuration; selectively moving at least the portion of the device into an expanded configuration to position the transducer elements at least proximate the non-fluid tissue; selectively moving at least the portion of the device into the unexpanded configuration; and intravascularly retrieving the device from the desired position while at least a portion of the device is in the unexpanded configuration.

At least one embodiment may be summarized as a medical system including a device positionable in at least a portion of a bodily organ (e.g., a heart), the device including a plurality of transducer elements, at least some of the transducer elements responsive to at least one characteristic indicative of a presence of either a fluid (e.g., blood) or non-fluid tissue (e.g., wall of heart) a computing system having at least one processor and at least one memory that stores instructions, the computing system configured to computationally discriminate between the fluid and the non-fluid tissue based at least in part on the at least one characteristic sensed by at least some of the transducer elements; and at least one transducer configured to provide information indicative of at least a position of the device in the bodily organ based on the computational discrimination between the fluid and the non-fluid tissue.

The system may further include an ablation source, wherein at least some of the transducer elements may be coupled to an ablation source and selectively operable to ablate a portion of the non-fluid tissue in the heart. At least some of the transducer elements that are responsive to at least one characteristic indicative of a presence of either the fluid or the non-fluid tissue in the bodily organ may also be responsive to electrical potential of the non-fluid tissue. At least some of the transducer elements may be responsive to electrical potentials of the non-fluid tissue, and the computing system may be further configured to produce an indication indicative of whether the ablation was successful based on at least one sensed electrical potential of the non-fluid tissue. At least a portion of the device may be selectively moveable between an unexpanded configuration and an expanded configuration, the device sized to be delivered intravascularly when at least the portion of the device is in the unexpanded configuration, and the transducer elements positioned sufficient proximate the non-fluid tissue to sense the at least one characteristic in the expanded configuration. The system may further include a catheter having a proximal end and a distal end opposed to the proximal end, the device coupled to the catheter at the distal end thereof; at least one communications path communicatively coupling the transducer elements and the computing system, the communications path including a multiplexer and a demultiplexer, the multiplexer on a computing system side of the communications path and the demultiplexer on a device side of the communications path.

At least one embodiment may be summarized as a method of operating a device in at least a portion of a heart, including sensing at least one characteristic by each of a number of transducer elements carried by the device located in at least the portion of the heart, the at least one characteristic indicative of at least one of a presence of blood and a presence of non-blood tissue; computationally discriminating between the blood and the non-blood tissue based at least in part on the at least one characteristic sensed by at least some of the transducer elements; providing information indicative of a position of the device in the heart based on the discrimination between the blood and the non-blood tissue; sensing an electrical potential of the non-blood tissue in the heart; and providing an indication based on the sensed electrical potential of the non-blood tissue.

The method may further include ablating a portion of the tissue in the heart, wherein sensing an electrical potential of the non-blood tissue in the heart may occur at least once after the ablating. The method may further include evaluating the sensed electrical potential of the non-blood tissue in the heart to determine whether the ablating was successful.

At least one embodiment may be summarized as a medical system including a device positionable in at least a portion of a heart, the device including a plurality of transducer elements at least some of the transducer elements responsive to at least one characteristic indicative of at least one of a presence of blood and a presence of non-blood tissue and at least some of the transducer elements responsive to an electrical potential of the non-blood tissue in the heart; a computing system having at least one processor and at least one memory that stores instructions, the computing system configured to computationally discriminate between the blood and the non-blood tissue based at least in part on the at least one characteristic sensed by at least some of the transducer elements; and at least one transducer configured to provide information indicative of a position of the device in the heart based on the computational discrimination between the blood and the non-blood tissue and provide an indication based on the sensed electrical potential of the non-blood tissue.

The system may further include an ablation source, wherein at least some of the transducer elements may be coupled to an ablation source and selectively operable to ablate a portion of the non-fluid tissue in the heart. The system may further include a switch operable to selectively couple the transducer elements between an ablation mode and a sense mode, where the transducer elements may ablate the non-blood tissue in the ablation mode and may sense the at least one characteristic in the sense mode. At least some of the transducer elements that are responsive to at least one characteristic indicative of a presence of either blood or non-blood tissue may also be responsive to electrical potential of the non-blood tissue. At least a portion of the device may be selectively moveable between an unexpanded configuration and an expanded configuration, the device sized to be delivered intravascularly when at least the portion of the device is in the unexpanded configuration, and the device sized to position the transducer elements sufficiently proximate the non-blood tissue to sense the at least one characteristic in the expanded configuration. The transducer elements may include at least one of a conductive trace on a flexible electrically insulative substrate, a conductive wire, a conductive tube, a carbon fiber material and a polymeric piezoelectric material. The device may include a number of flexible electrically insulative substrates that deform between an unexpanded configuration and an expanded configuration.

At least one embodiment may be summarized as a device to be inserted intravascularly, including a shaft moveable with respect to a catheter member; at least a first helical member configured to move between a radially unexpanded configuration and a radially expanded configuration in response to the movement of the shaft with respect to the catheter, the device sized to be delivered intravascularly when at least the first helical member is in the unexpanded configuration; and a plurality of transducer elements that move in response to the movement of the first helical member between the radially unexpanded configuration and the radially expanded configuration, at least some of the transducer elements responsive to a characteristic of at least one of a fluid and a non-fluid tissue.

The device may further include at least a second helical member configured to move between a radially unexpanded configuration and a radially expanded configuration in response to the movement of the shaft with respect to the catheter. The first helical member may carry some of the transducer elements and the second helical member may carry some of the transducer elements. The first helical member may be disposed radially spaced about the shaft. The first helical member may be wound in one of a clockwise or a counterclockwise orientation with respect to the shaft and the second helical member may be wound in the other of the clockwise or the counterclockwise orientation with respect to the shaft. The device may further include a number of elongated ribs physically coupled between a proximate and a distal end of the first helical member. The elongated ribs may each form a respective flexible electrically insulative substrate and at least some of the transducer elements may comprise respective electrically conductive traces carried by the flexible electrically insulative substrate. The shaft may be axially moveable with respect to the catheter member between an extended position and a withdrawn position, a distal end of the shaft spaced relatively closer to an end of the catheter member in the withdrawn position than in the extended position, where the first helical member is in the unexpanded configuration when the shaft is in the extended position and is in the expanded configuration when the shaft is in the withdrawn position. The shaft may be rotatably moveable with respect to the catheter member between an extended position and a withdrawn position, a distal end of the shaft spaced relatively closer to an end of the catheter member in the withdrawn position than in the extended position, where the first helical member is in the unexpanded configuration when the shaft is in the extended position and is in the expanded configuration when the shaft is in the withdrawn position. The shaft may extend at least partially through a lumen of the catheter member to allow manipulation of the device from a position externally located from a patient. At least some of the transducer elements may be responsive to convective cooling from a flow of blood over the transducer elements. At least some of the transducer elements may be responsive to a permittivity at each of a plurality of frequencies. At least some of the transducer elements may be responsive to a force. At least some of the transducer elements may comprise a polymeric piezoelectric material. At least some of the transducer elements may be responsive to an electrical potential of a portion of the non-blood tissue. At least some of the transducer elements may include an electrically conductive trace carried by a flexible electrically insulative substrate. The first helical member may form a flexible electrically insulative substrate and at least some of the transducer elements may comprise respective electrically conductive traces carried by the flexible electrically insulative substrate. At least some of the transducer elements may include an electrically conductive wire. At least some of the transducer elements may include an electrically conductive tube. At least some of the transducer elements may include an electrically conductive carbon fiber.

At least one embodiment may be summarized as a method of operating a device including at least a first helical member and a plurality of transducer elements that are responsive to at least one characteristic of non-blood tissue, comprising: guiding a device in an unexpanded configuration intravascularly to a desired position; and expanding at least the first helical member of the device into an expanded configuration such that the plurality of transducer elements are positioned to sense the at least one characteristic over a substantial portion of the non-blood tissue.

The expanding at least the first helical member may include axially moving a shaft that extends at least partially through a lumen of a catheter member in a first direction. The expanding at least first helical member may include rotatably moving a shaft that extends at least partially through a lumen of a catheter member in a first direction. The method may further include retracting at least the first helical member into the unexpanded configuration; and intravascularly guiding the device in the unexpanded configuration to remove the device. The retracting at least the first helical member into the unexpanded configuration may include at least one of axially or radially moving the shaft that extends at least partially through the lumen of the catheter member in an opposite direction than moved when expanded.

At least one embodiment may be summarized as a medical device, including at least a first inflatable member having at least one chamber and at least one port that provides fluid communication with the chamber, the first inflatable member configured to move between an unexpanded configuration and an expanded configuration in response to a change of a pressure in the chamber, the device sized to be delivered intravascularly when at least the first inflatable member is in the unexpanded configuration; a plurality of transducer elements that move in response to the movement of the first inflatable member between the radially unexpanded configuration and the radially expanded configuration, at least some of the transducer elements responsive to a characteristic of at least one of a fluid and a non-fluid tissue.

The first inflatable member may have at least one passage that provides fluid communication across the first inflatable member. The at least one passage may provide fluid communication between an upstream position and a downstream position with respect to a position of the inflatable member when positioned in a cardiovascular structure. The at least one passage may be formed by a reinforced portion of the first inflatable member. The reinforced portion of the first inflatable member may include at least a rib, an elastic member, and a thickened portion of a wall that forms the passage. The port may be coupled to a lumen of a catheter member to allow fluid communication with the chamber from a fluid reservoir that is externally located with respect to a patient. At least some of the transducer elements may be responsive to convective cooling from a flow of blood over the transducer elements. At least some of the transducer elements may be responsive to a permittivity at each of a plurality of frequencies. At least some of the transducer elements may be responsive to a force. At least some of the transducer elements may comprise a polymeric piezoelectric material. At least some of the transducer elements may be responsive to an electrical potential of a portion of the non-blood tissue. At least some of the transducer elements may include an electrically conductive trace carried by a flexible electrically insulative substrate. The first helical member may form a flexible electrically insulative substrate and at least some of the transducer elements may comprise respective electrically conductive traces carried by the flexible electrically insulative substrate. At least some of the transducer elements may include an electrically conductive wire. At least some of the transducer elements may include an electrically conductive tube. At least some of the transducer elements may include an electrically conductive carbon fiber.

At least one embodiment may be summarized as a method of operating a device including at least a first inflatable member and a plurality of transducer elements that are responsive to at least one characteristic of non-blood tissue, comprising: guiding a device in an unexpanded configuration intravascularly to a desired position; and inflating at least the first inflatable member of the device into an expanded configuration such that the plurality of transducer elements are positioned to sense the at least one characteristic over a substantial portion of the non-blood tissue.

Inflating at least the first helical member may include providing a fluid to a chamber of the first inflatable member through a lumen of a catheter member. The method may further include deflating at least the first inflatable member into the unexpanded configuration; and intravascularly guiding the device in the unexpanded configuration to remove the device. Deflating at least the first helical member into the unexpanded configuration may include removing the fluid from the chamber through the lumen of the catheter member.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 4A is a top plan view of element construction for flow sensing.

FIG. 4B is a top plan view according to yet another illustrated embodiment

FIG. 4C is a top plan view according to yet another illustrated embodiment.

FIG. 4D is a top plan view according to yet another illustrated embodiment.

FIG. 4E is a top plan view according to yet another illustrated embodiment.

FIG. 4F is a top plan view according to yet another illustrated embodiment.

FIG. 4G is a top plan view according to yet another illustrated embodiment.

FIG. 4H is a top plan view according to yet another illustrated embodiment.

FIG. 5 is a diagram showing how common leads can be shared by elements used for flow sensing.

FIG. 6A is a schematic diagram showing an example of techniques used to improve precision in measuring voltage drops across elements.

FIG. 6B is a schematic diagram showing an example of techniques used to improve precision in measuring voltage drops across elements.

FIG. 6C is a schematic diagram showing an example of techniques used to improve precision in measuring voltage drops across elements.

FIG. 12A is a top plan view of a structure having distinct force sensor elements, temperature sensor elements and ablation elements, according to one illustrated embodiment.

FIG. 12B is top plan view of a structure having force sensor elements that are distinct from integrated temperature sensor and ablation elements, according to one illustrated embodiment.

FIG. 12C is a top plan view of a leaf shaped structure having force sensor elements that are distinct from integrated temperature sensor and ablation elements, according to one illustrated embodiment.

FIG. 15A is an example of a frame using a single helix shaped member and multiple ribs.

FIG. 15B is an example of a frame using a single helix shaped member and multiple ribs FIG. 15C is an example of a frame using a single helix shaped member and multiple ribs.

FIG. 16A is an example of an inflatable frame with ports for blood flow.

FIG. 16B is an example of an inflatable frame with ports for blood flow.

DETAILED DESCRIPTION OF THE INVENTION

Figure 1:
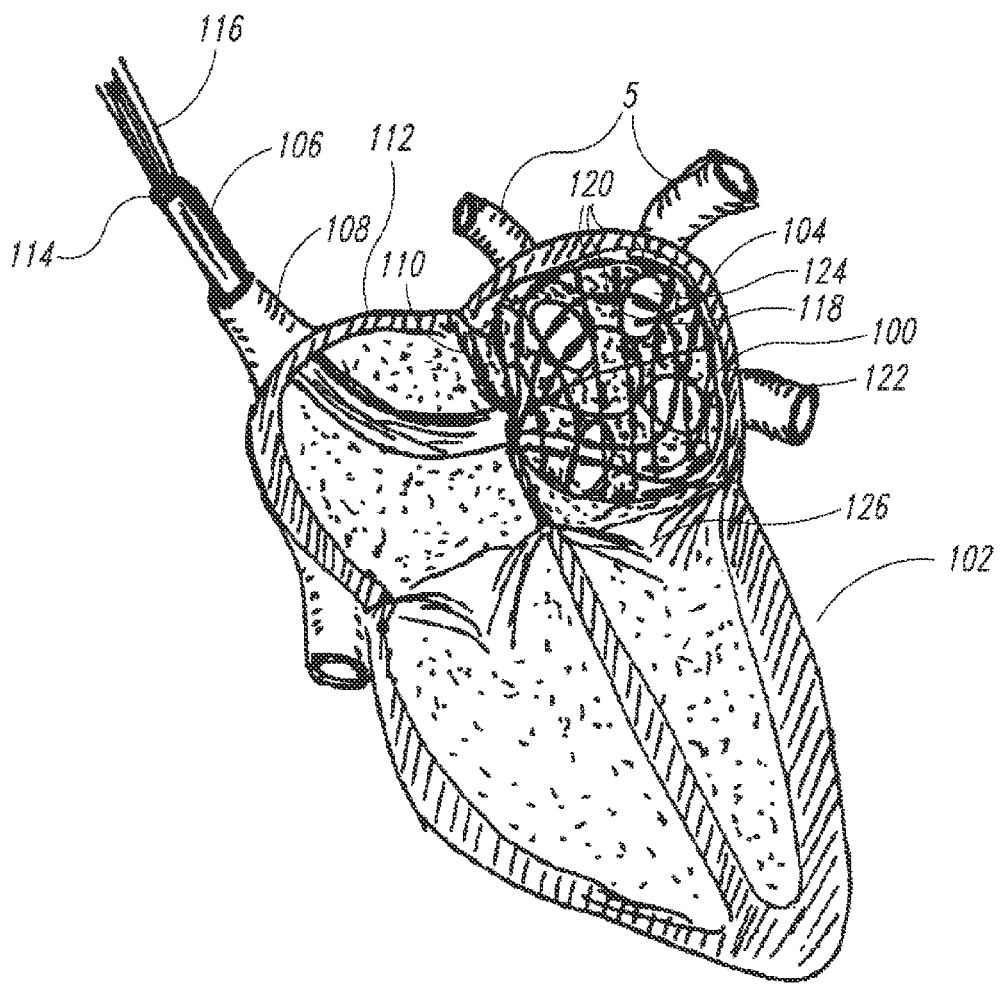
FIG. 1 is a cutaway diagram of a heart showing a medical device according to one illustrated embodiment percutaneously placed in a left atrium of the heart.

In the following description, certain specific details are set forth in order to provide a thorough understanding of various embodiments of the invention. However, one skilled in the art will understand that the invention may be practiced without these details. In other instances, well-known structures associated with RF ablation and electronic controls such as multiplexers have not been shown or described in detail to avoid unnecessarily obscuring descriptions of the embodiments of the invention.

Unless the context requires otherwise, throughout the specification and claims which follow, the word "comprise" and variations thereof, such as, "comprises" and "comprising" are to be construed in an open, inclusive sense, that is as "including, but not limited to."

The word "ablation" should be understood to mean any disruption to certain properties of the tissue. Most commonly the disruption is to the electrical conductivity and is achieved by heating, which could be either resistive or by use of Radio Frequencies (RF). Other properties, such as mechanical, and other means of disruption, such as optical, are included when the term "ablation" is used.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The headings provided herein are for convenience only and do not interpret the scope or meaning of the claimed invention.

Overview of Device and Mapping Methods

Various embodiments of percutaneously or intravascularly deployed medical devices are described herein. The medical devices are capable of expanding into a cavity within a body and sensing characteristics (e.g., convective cooling, permittivity, force) that distinguish between blood and non-blood tissue. Such sensed characteristic allow a medical system to map the cavity, for example using positions of openings or ports into and out of the cavity to determine a position and/or orientation (i.e., pose) of the medical device in the cavity. The medical devices may also be capable of ablating tissue in a desired pattern within the cavity. The medical devices may further be capable of sensing characteristics (e.g., electrical activity), indicative of whether ablation has been successful.

An example of the mapping performed by the medical treatment devices would be to locate the position of the four openings leading to the pulmonary veins as well as the mitral valve on the interior surface of the left atrium. The mapping is based on locating such openings by differentiating between blood and non-blood tissue. There are many ways to differentiate non-blood tissue from a liquid such as blood or to differentiate non-blood tissue from an opening in case a liquid is not present. By the way of example, three approaches will be detailed in the disclosure:

1. One approach to determining the locations is to use the convective cooling of heated transducer elements by the blood. A slightly heated mesh of transducer elements positioned adjacent to the non-blood tissue that forms walls of the atrium and across the openings or ports of the atrium will be cooler at the areas which are spanning the openings or ports carrying blood flow.

2. Another approach to determining the locations is to make use of the differing change in dielectric constant as a function of frequency between blood and non-blood tissue. A set of transducer elements positioned around the non-blood tissue that forms the interior surface of the atrium and across the openings or ports of the atrium monitor the ratio of the dielectric constant from 1 KHz to 100 KHz. Such can be used to determine which of those transducer elements are not proximate to non-blood tissue, which is indicative of the locations of openings or ports.

3. Yet another approach to determining the locations is to sense a position of the non-blood tissue that forms the atrium walls using transducer elements that sense force (i.e., force sensors). A set of force detection transducer elements positioned around the non-blood tissue that forms the interior surface of the atrium and across the openings or ports of the atrium can be used to determine which of the transducer elements are not in contact with the non-blood tissue, which is indicative of the locations of openings or ports.

FIG. 1 shows a medical device 100 useful in diagnosing and/or treating a bodily organ, for example a heart 102, according to one illustrated embodiment.

The medical device 100 may be percutaneously and/or intravascularly inserted into a portion of the heart 102, for example in a left atrium 104 of the heart 102. In this example, the medical device is delivered via a catheter 106 inserted via the superior vena cava 108 and penetrating the transatrial septum 110 from a right atrium 112.

The catheter 106 may include one or more lumens 114. The lumen(s) 114 may carry one or more communications and/or power paths, for example one or more wires 116. The wires 116 provide connections to the medical device 100 that are accessible externally from a patient in which the medical device 100 is inserted.

As discussed in more detail herein, the medical device 100 comprises a frame 118 which expands (shown in expanded configuration in FIG. 1) upon delivery to the left atrium 104 to position a plurality of transducer elements 120 (only three called out in FIG. 1) proximate the interior surface or non-blood tissue 122 of the left atrium 104. At least some of the transducer elements 120 of the medical device are used to sense a physical characteristic of blood and/or tissue that may be used to determine a position and/or orientation or pose of the medical device 100 in the left atrium 104. For example, the transducer elements 120 may be used to determine a location of pulmonary vein ostiums 124 and/or a mitral valve 126. At least some of the transducer elements 120 of the medical device 100 may be used to selectively ablate non-blood tissue, for example portions of the interior surface 122 of the left atrium 104. For example, some of the elements may be used to ablate a pattern around the openings, ports or pulmonary vein ostiums 124, for instance to reduce or eliminate the occurrence of atrial fibrillation.

Figure 2:
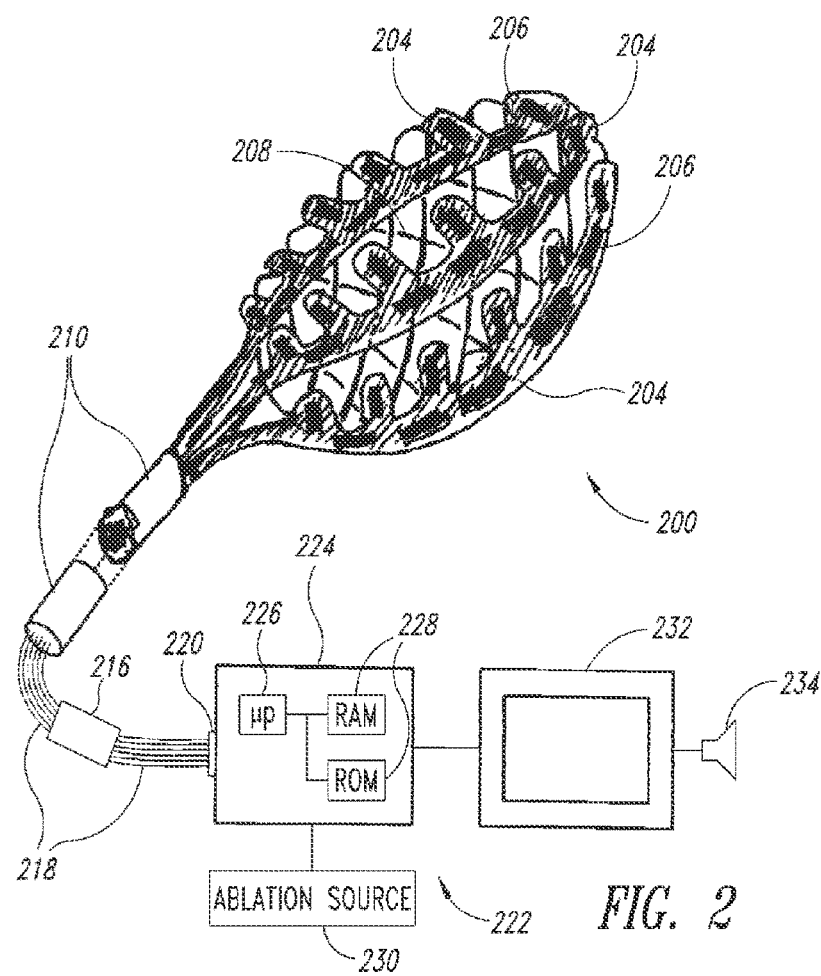
FIG. 2 is a schematic diagram of a treatment system according to one illustrated embodiment, including, a control unit, a display, and a medical device having an expandable frame and a leaf shaped assembly of elements.

FIG. 2 shows a medical device 200 according to one illustrated embodiment.

The medical device 200 takes the form of an expandable electrode grid or array 202, including a plurality of flexible strips 204 (three called out in FIG. 2). A plurality of transducer elements 206 (four called out in FIG. 2) form a two- or three-dimensional grid or array capable of mapping the inside surface of a cavity or lumen without requiring mechanical scanning. An expandable frame 208 may be used to force flexible strips 204 against the inside walls of the cavity. The expandable frame 208 may include one or more resilient members. For example, the expandable frame 208 may consist of or include a shape memory material, for instance Nitinol. Such may be useful for both accurate location of the parts, position and/or orientation (i.e., pose) and/or for successful ablation of a desired pattern.

The expandable frame 208, as well as flexible strips 204 can be delivered and retrieved via a catheter member, for example a catheter sheath introducer 210, which in some embodiments may have a diameter of about 8 mm or smaller. Flexible strips 204 may be made of one or more thin layers of Kapton (polyimide), for instance 0.1 mm thick. Transducer elements (e.g., electrodes and/or sensors) 206 may be built on the flexible strips 204 using standard printed circuit board processes. An overlay of a thin electrical insulation layer (e.g., Kapton about 10-20 microns thick) may be used to provide electrical insulation, except in areas needing electrical contact to blood and non-blood tissue. In some embodiments, the flexible strips 204 can form an elongated cable 216 of control leads 218, for example by stacking multiple layers, and terminating in a connector 220. The electrode grid or array 202 is typically disposable.

The medical device 200 may communicate with, receive power from and/or be controlled by a control system 222. The control system 222 may include a computing system 224 having one or more processors 226 and one or more memories 228 that store instructions that are executable by the processors 226 to process information received from the medical device 200 and/or to control operation of the medical device 200, for example activating selected transducer elements 206 to ablate non-blood tissue. The control system 222 may include an ablation source 230. The ablation source 230 may, for example, provide electrical power, light or low temperature fluid to the selected transducer elements to cause ablation. The control system 222 may also include one or more user interface or input/output (I/O) devices, for example one or more displays 232, speakers 234, keyboards, mice, joysticks, track pads, touch screens or other transducers to transfer information to and from a user, for example a care provider such as a medical doctor or technician. For example output from the mapping process may be displayed on a display 232.

While the disclosed systems are described with examples of cardiac mapping, the same or similar systems may be used for mapping other bodily organs, for example gastric mapping, bladder mapping, arterial mapping and mapping of any lumen or cavity into which the medical device 204 may be introduced.

The term "transducer element" in this disclosure should be interpreted broadly as any component capable of distinguishing between blood and tissue, sensing temperature, creating heat, ablating tissue and measuring electrical activity of a non-blood tissue surface, or any combination thereof. A transducer element may be constructed from several parts, which may be discrete components or may be integrally formed.

Sensing Convective Cooling

Figure 3:
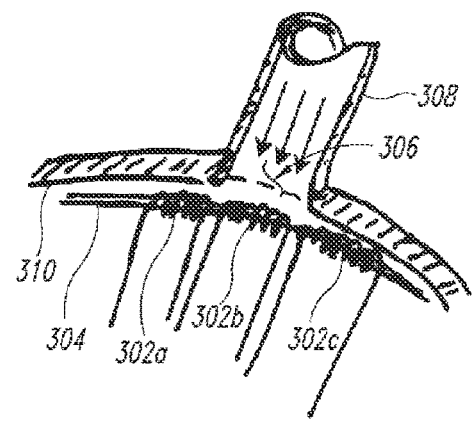
FIG. 3 is a broken isometric diagram of a portion of an atrium and a number of elements showing how the elements can sense convective cooling to locate a position of ports.

FIG. 3 shows a portion of a medical device 300, according to one illustrated embodiment.

The portion of the medical device 300 is particularly suitable to sense convective cooling. The medical device 300 includes miniature transducer elements 302a, 302b, 302c (collectively 302) capable of producing heat. The transducer elements 302 may, for example, be made of insulated resistive wire, such as Nickel, or Nickel-iron composition. The resistive wire may be mounted on an expandable frame 304. In this embodiment, the expandable frame 304 may also be made of a material that has high impedance. Current passed through each transducer element 302 raises the temperature of the transducer element 302 by a nominal amount. A rise of 0.5-3.0 degrees Celsius above normal blood temperature has been found to be sufficient in most cases. The power required to raise the temperature in this particular embodiment is about 10-50 mW per transducer element 302. A central one of the transducer elements 302b, which is placed across the opening, port of ostium 306 of the pulmonary vein 308 will be cooled by blood flow more than the neighboring transducer elements 302a, 302c which are adjacent to the inner or interior surface or non-blood tissue 310 that forms the wall of the heart. Transducer elements 302 which are found to be cooler on expandable frame 304 indicate the locations of openings or ports 306 in the non-blood tissue 310 that forms the wall of the heart. This embodiment does not require intimate contact with the bodily tissue 310 of the heart wall, as even a few millimeters from the openings or ports 306 the cooling effect is significant compared to the cooling effect a few millimeters from the non-blood tissue 310 of the heart wall. The back side of the transducer elements 302 may be thermally insulated for improved performance of both sensing and ablation. Using a flat ribbon for the expandable frame 304 may be advantageous. A cross section of a ribbon expandable frame 304 may, for example have dimensions of 0.2×2 mm for stainless steel or 0.3×2.5 mm for Nitinol. The insulation on the back side of the transducer elements 302 may take the form of a coat of silicone rubber.

If the transducer elements 302 are made of a material that has a significant change in resistance with temperature, the temperature drop can be determined from the resistance of the transducer element 302. The resistance can be determined by measuring the voltage across the transducer element 302 for a given current, or alternatively by measuring the current across the transducer element 302 for a given voltage, for example via a Wheatstone bridge circuit. Thus, some embodiments may take advantage of convective cooling by the flow of blood, at least some of the transducer elements 302 functioning as a hot wire anemometer. Nickel wire is a suitable material to use, as nickel is inert, highly resistive and has a significant temperature coefficient of resistance (about 0.6% per deg C). Since the resistance of the transducer elements 302 is low (typically less than 5 ohm), the electrical noise is very low and temperature changes as low as 0.1-1 deg can be detected. There are several techniques to improve on this sensitivity. One method is to sample the voltage waveform in synchronization with the heart rate. Another is to remove the average voltage via AC coupling and only amplify the voltage change or derivative. Yet another method to reduce the electrical noise is to pass the signal through a digital band pass filter having a center frequency tracking the heart rate.

FIGS. 4A-4G show examples of alternative ways of constructing transducer elements. Each of the embodiments of FIGS. 4A-4F show transducer elements which have been constructed using printed circuit board (PCB) substrates. These transducer elements may be affixed to a structure similar to the expandable frame 208 shown in FIG. 2, which may be made from a material such as Nitinol. Alternatively, the PCB substrates may be of such a thickness that the PCB substrates can form the expandable frame. The PCB substrates should be flexible enough to conform to the non-blood tissue, but stiff enough such that the PCB substrate does not buckle. PCB substrates may, for example, be made from Kapton®. A PCB substrate made of Kapton® having a thickness, for instance, of approximately 0.1 to 0.3 mm may be suitable. The transducer elements could also be constructed using discrete components. FIGS. 4G-4H show embodiments that do not employ PCB substrates.

FIG. 4A shows a PCB substrate 400a that carries a combination of transducer elements, in particular sensor transducer elements 402a, 402b (collectively 402, only two called out in FIG. 4A) which sense convective cooling and ablation transducer elements 404a, 404b (collectively 404, only two called out in FIG. 4A) which are operable to ablate non-blood tissue. Leads, collectively 406, extend to respective ones of the transducer elements 402, 404. The leads 406 may be coupled to a control system (e.g., control system 222 of FIG. 2), which may provide communications, power and/or control with the transducer elements 402, 404.

FIG. 4B shows a PCB substrate 400b that carries a number of combined sensor and ablation transducer elements 408a, 408b (collectively 408, only two called out in FIG. 4B) that both sense flow and ablate non-blood tissue. Such a feature may be a significant advantage since a medical device with combined sensor and ablation transducer elements 408 can measure flow at the exact spot that ablation will occur, while requiring fewer parts, thus improving precision and reducing size. In this embodiment, each combined sensor and ablation transducer element 408 has respective leads, collectively 410, coupled to a control system (e.g., control system 222 of FIG. 2).

A combined sensor and ablation transducer element 408 that can be used for both sensing flow and ablating can be made using standard PCB construction processes. For example, a 2-4 mil copper trace on a Kapton® substrate can be used. Copper changes resistance sufficiently with temperature to be used to determine blood flow in the manner discussed above. Copper can also be used as an ablation element by applying sufficient current through the copper to cause the combined sensor and ablation transducer element 408 to heat resistively, for example to a temperature above 60° C. Power in the range of approximately 130-250 mW delivered to a copper pattern that has external dimensions of 3 mm×10 mm and is thermally insulated on the side away from the non-blood tissue may be sufficient to transmurally ablate a 3 mm deep section of the non-blood tissue that forms the atrium wall. In this approach, the non-blood tissue is heated by conduction from the copper combined sensor and ablation transducer element 408. When heating the non-blood tissue by conduction, the combined sensor and ablation transducer element 408 may be electrically insulated from the non-blood tissue.

Alternatively, the combined sensor and ablation transducer element 408 can also be used to ablate non-blood tissue by using the combined sensor and ablation transducer element 408 as an electrode for delivering RF energy to the non-blood tissue. In this scenario, electrical current is transferred directly to the non-blood tissue and the non-blood tissue is resistively heated by the current flow. When delivering RF energy, a preferred method may be to have low electrical impedance between the combined sensor and ablation transducer element 408 and the non-blood tissue. Delivering RF energy is also possible if the combined sensor and ablation transducer element 408 is capacitively coupled to the non-blood tissue, so long as the impedance at the frequency of RF energy being used is sufficiently low—typically under a few kilo ohms or less for a combined sensor and ablation transducer element of the size mentioned above. Note that in the case where the combined sensor and ablation transducer element 408 has a low electrical impedance connection to the non-blood tissue for low frequencies, it is also possible to use the combined sensor and ablation transducer element 408 to sense an electrical potential in the non-blood tissue that forms the heart wall, for example to generate an electro-cardiogram. Thus it is possible for the same combined sensor and ablation transducer element 408 to sense flow, sense electrical potential of the non-blood tissue that forms the heart wall, and ablate non-blood tissue.

FIG. 4C shows a PCB substrate 400c that carries a number of combined flow sensor, ablation and temperature transducer elements 412a, 412b (collectively 412, only two called out in FIG. 4C) that can be used to sense flow, ablate non-blood tissue and sense or monitor temperature, for example for ablation control. A single control lead, collectively 414, is required per combined flow sensor, ablation and temperature transducer element 412, plus a common return lead 416 to the multiple combined flow sensor, ablation and temperature transducer elements 412. The combined flow sensor, ablation and temperature transducer element 412 can take the form of a low resistance resistor, for example a resistor formed by a 30-100 micron wide trace of 10-30 micron copper foil. Such a resistor has a typical resistance of 2-20 ohms and can be used as a combined flow sensor, ablation and temperature transducer element 412 to sense flow, perform ablation and sense temperature. When used as a temperature sensor, the resistance changes about 1% for a 2 degree C. temperature change.

FIG. 4D shows a PCB substrate 400d that carries a number of adjacent transducer elements 420a, 420b (collectively 420, only two called out in FIG. 4D). The transducer elements 420 share common control leads 422. This feature is an advantage as it dramatically reduces the number of leads 422 needed to return to the control system (e.g., control system 222 of FIG. 2).

FIG. 5 shows an expanded example of a portion of the embodiment of FIG. 4D positioned proximate non-blood tissue 500. To determine flow by measuring the resistance of transducer element 420b, the voltage at a lead 422a and lead 422b should be made equal and the voltage at a lead 422c and lead 422d should be made equal, but to a different voltage than that of lead 422a and lead 422b. In this condition, negligible current will flow through transducer element 420a and transducer element 420c. Therefore, the current flowing through lead 422b and lead 422c is the same as the current flowing through the transducer element 420b, and the resistance of the transducer element 420b can be calculated in a straightforward manner using the equation V=I/R.

To cause the transducer element 420b to heat to a temperature sufficient to cause ablation, while not causing ablation at transducer element 420a and transducer element 420c:

the voltage at lead 422c and lead 422d should be made equal;
the voltage at lead 422b should be made higher than the voltage at lead 422c such that sufficient power is delivered to the transducer element 420b to cause the transducer element 420b to heat to the appropriate temperature; and the voltage at lead 422a should be set a value that is a fraction of that at lead 422b such that the power delivered to the transducer element 420a is not sufficient to cause the temperature of the transducer element 420a to rise enough for tissue ablation.

For example, if the voltages at lead 422c and lead 422d are set to 0 v, voltage at lead 422b is set to n volts and voltage at lead 422a is set to ⅔ n volts, the power delivered to the transducer element 420a will be only 11% of that delivered to the transducer element 420b. This technique of having adjacent transducer elements 420 share common leads 422 can, for example, be used in a elongated one-dimensional line of connected transducer elements 420 or may be applied to transducer elements 420 connected in two-dimensional (as illustrated in FIGS. 8, 17A-17C, 18A and 18B) or three-dimensional arrays.

FIG. 4E shows a PCB substrate 400e that carries a number of transducer elements 424a, 424b (collectively 424, only two called out in FIG. 4E). The transducer elements 424 are coupled to leads 426, similar to leads 422 of the embodiment of FIG. 4D, and to additional leads 428, which have been added to measure the voltage at the ends of the transducer elements 424. This feature advantageously increases the accuracy in determining the resistance, and thus temperature, of the transducer elements 424. The leads 426 that provide the current to the transducer elements 424 typically have a small voltage drop across them that can affect the accuracy of the resistance calculation of the transducer element 424. These additional leads 428 will have a very limited amount of current flowing through them, and thus the voltage drop through the leads 428, even for a distance of several meters will be negligible, and the voltage drop across the transducer elements 424 can be determined accurately.

FIG. 4F shows a flexible PCB substrate 400f that forms a leaf shaped assembly. An expandable frame (e.g., expandable frame 208 of FIG. 2) may be covered by several of these leaf shaped assemblies, each of which will cover or be proximate a respective portion of the non-blood tissue that forms the wall of the body organ when in use. Each of the leaf shaped assemblies caries a plurality of transducer elements 430a, 430b (collectively 430, only two called out in FIG. 4F). In this example, the transducer elements 430 are coupled together as described above embodiment of FIG. 4D. Leads 432 couple each transducer 430 to a control system (e.g., control system 222 of FIG. 2). The leads 432 may couple power, communications and/or control signals. The leads 432 may, for example, provide for electrically conductive coupling, inductive coupling, capacitive coupling, optical coupling, galvanic coupling, fluidic coupling and/or thermal coupling.

There are other approaches for creating the transducer elements that do not rely on a PCB. FIGS. 4G and 4H provide examples of some of these.

FIG. 4G shows transducer elements 440a, 440b (collectively 440, only two called out in FIG. 4G) that are made from a bundle of carbon fibers. Leads 442 couple the transducer elements 440 to a control system.

FIG. 4H shows transducer elements 450a, 450b (collectively 450, only two called out in FIG. 4H) that are made directly from a hollow tube of a metal such as stainless steel or alternatively from wire. Leads 452 couple the transducer elements 450 to a control system.

The structures of the embodiments of FIGS. 4G and 4H may be advantageous over other embodiments, since the structures are simple to assemble, and can be used directly as the supporting structure itself. Leads 442, 452 are connected at intervals to the carbon fibre or metal. The material between the leads 442, 452 form the transducer elements 440, 450. In order to function properly, these transducer elements 440, 450 should have the electrical properties the same as or similar to the electrical properties indicated previously. These two embodiments provide an example of where the same transducer element 440, 450 can sense flow, sense or measure temperature, deliver the ablation energy, and/or be an integral component of the supporting structure.

FIGS. 4A-4H show examples of many transducer element configurations that are possible. From the previous descriptions, it is important to note that a single transducer element can sense blood flow in order to distinguish between blood and non-blood tissue, sense an electrical potential of the non-blood tissue (e.g., heart wall), ablate non-blood tissue, sense or measure temperature, and/or form an integral component of the supporting structure, or any combination of these functions. The ablation may be performed by causing the transducer element to heat, or by delivering energy, such as RF directly to the non-blood tissue. Also, transducer elements can be constructed using individual leads, common ground lead, or shared leads. Each lead may have a separate lead that runs in parallel to it for the purpose of accurately determining voltage potential directly at the transducer element. As well, the examples discussed methods of sensing temperature that relied on changes in resistance. However, it is certainly possible to use other temperature sensing methods, such as thermistors or thermocouples in conjunction with the transducer elements that produce heat. For example, the sensing transducer element of the embodiment of FIG. 4A could be a thermistor, thermocouple or temperature sensitive diode.

Figure 7:
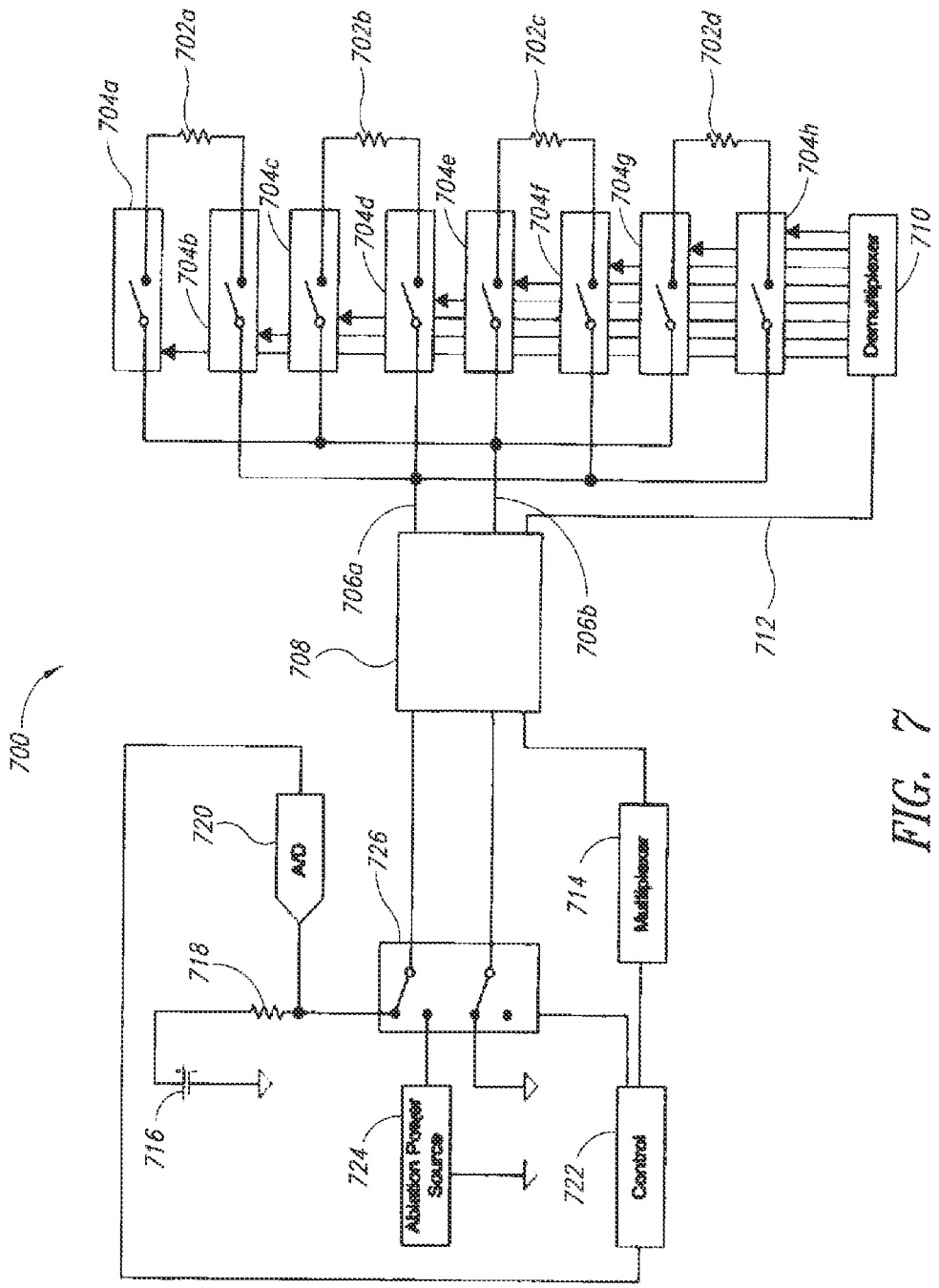
FIG. 7 is a circuit diagram of an example of a system used for flow sensing, port location, and tissue ablation.

FIG. 7 shows an embodiment of an electric circuit 700 that can be used to distinguish between blood and non-blood tissue by sensing flow of blood.

In this example, transducer elements 702a-702d (collectively 702) may be resistive elements, for example formed from copper traces on a flexible printed circuit board substrate, or resistive wires mounted on a structure. Each transducer element 702 is connected by electronic transducer selection switches 704a-704h (collectively 704) to a single pair of wires 706a, 706b (collectively 706) that provide a path out of the body via a cable 708. The transducer selection switches 704 may, for example be FET or MOSFET type transistors. The transducer selection switches 704 will typically need to carry significant power during the ablation phase. The cable 708 may extend through a lumen of a catheter or may otherwise form part of a catheter structure.

The transducer selection switches 704 are selected by signals applied by a demultiplexer (selector) 710. The demultiplexer 710 may be controlled by a small number of wires 712 (or even a single wire if data is relayed in serial form). The wires 706, 712 extend out of the body via the cable 708. The transducer selection switches 704 and the demultiplexer 710 may be built into a catheter (e.g., catheter 106 of FIG. 1) near a distal end or point of deployment. The transducer selection switches 704 and demultiplexer 710 may be located within or near the expandable frame (e.g., expandable frame 208 of FIG. 2) in order to minimize the number and/or length of connecting wires extending through the catheter.

At the other or proximate end of the catheter are a mode selection switch 726 and multiplexer 714. The mode selection switch 726 is operable to select between a flow sensing mode (position shown in the drawing) and an ablation mode (second position of the mode selection switch 726). In flow sensing mode, a current is created by a voltage source 716 and resistor 718 (forming an approximate current source) and routed into a transducer element 702 selected via transducer selection switches 704. The two transducer selection switches 704 that are connected to a given one of the transducer elements 702 to be used to sense flow, are set to be closed and the remainder of the transducer selection switches 704 are set to be open. The voltage drop across the transducer element 702 is measured via an Analog-to-Digital converter (ADC) 720 and fed to the control computer 722.

It may be advantageous to use alternating current or a combination of alternating current and direct current for sensing and ablation. For example, direct current for ablation and alternating current for sensing. Alternating current approaches may also prevent errors from electrochemical potentials which could be significant if different metals come in touch with blood.

Determination of the location of the openings or ports into the chamber may be achieved by turning on all of transducer elements 702 sequentially or in groups and determining a temperature by measuring the resistance of each transducer element 702. A map of the temperature of the transducer elements 702 may be formed in control computer 722 or the control computer 722 may otherwise determine a position and/or orientation or pose of the device in the cavity. The transducer elements 702 with lower temperatures correspond to the openings or ports leading to the veins or valves.

When mode selection switch 726 is set to select ablation, an ablation power source 724 is connected sequentially to the transducer elements 702 that are selected by the control computer 722 by addressing the multiplexer 714, which in turn controls the transducer selection switches 704 via the demultiplexer 710. The ablation power source 724 may be an RF generator, or it may be one of several other power sources, several of which are described below. If ablation power source 710 is an RF generator, the configuration of FIG. 7 implies unipolar RF ablation, in which current is fed into the non-blood tissue and passes to a ground connected to the body. The current that passes through the non-blood tissue causes the non-blood tissue to heat. However, bipolar ablation can be used as well. Other sources of ablation can be used besides radio frequency. Frequencies from DC to microwaves can be used, as well as delivery of laser power via optical fibers or cryogenics via thin tubes. For laser ablation, the transducer selection switches 704 may take the form of optical switches. For cryogenic ablation, the transducer selection switches 704 take the form of suitable valves and/or actuators (e.g., solenoids). Alternatively, the bottom terminal of the lower switch of mode selection switch 726 may be coupled directly to ground. In this configuration, the ablation power source 724 can be configured to supply current with frequencies from DC to microwave, which will cause the selected transducer elements 702 to heat directly and produce ablation via thermal conduction.

During ablation it may be desirable to monitor the temperature of the non-blood tissue. The ideal temperature range for the non-blood tissue during ablation is typically 50-100° C. Since the example includes temperature monitoring as part of the blood flow sensing, the progress of ablation can be monitored by temporarily switching mode selection switch 726 to a temperature sensing position several times during the ablation.

Figure 8:
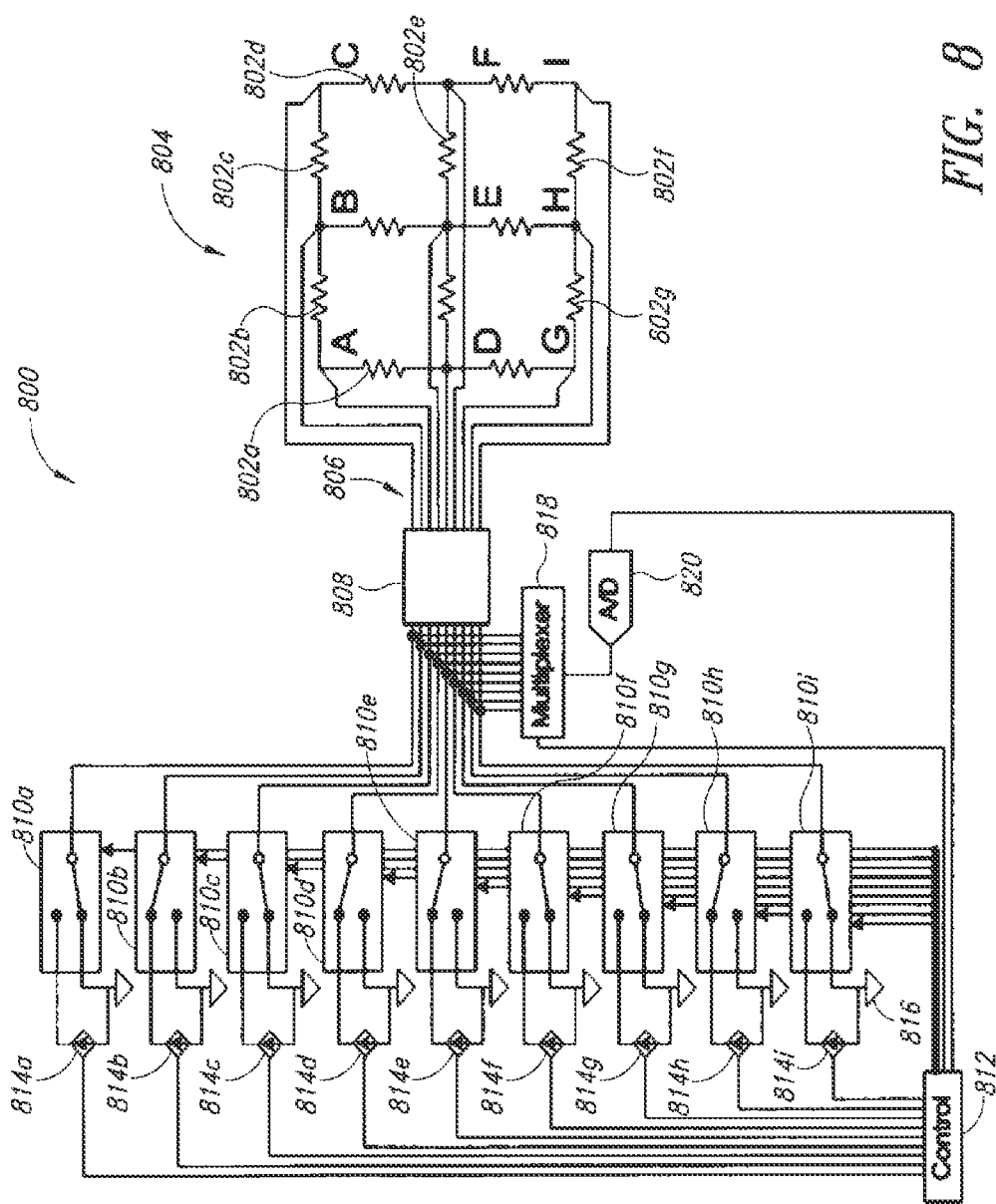
FIG. 8 is a circuit diagram of a second example of a system used for flow sensing, port location, and tissue ablation.

FIG. 8 shows another embodiment of a circuit 800 that can be used to distinguish between blood and non-blood tissue by sensing flow.

In this example, transducer elements 802*a*-802*g* (collectively 802, only seven called out in FIG. 8) may be resistive elements, for example formed from copper traces on a printed circuit board substrate, or resistive wires mounted on a structure. The ends of each transducer element 802 are electrically coupled to the ends of adjacent transducer elements 802 to form a connected grid or array 804. Each node (indicated in FIG. 8 by the markings A, B, C, D, E, F, G, H, and I) in the grid or array is electrically coupled to a respective control wire, collectively 806. The control wires 806 extend out of the human or animal body via a cable 808, which may, for example extend through a lumen of a catheter.

The control wires 806 may be coupled to respective ones of transducer selection switches 810*a*-810*i* (collectively 810) at a proximate end of a catheter. Each of the transducer selection switches 810 is controlled by a control system 812, which may, for example, take the form of a programmed general purpose computer, special purpose computer, applications specific integrated circuit (ASIC) or field programmable gate array (FPGA). The control system 812 applies signals to select between an adjustable current source 814*a*-814*i* (collectively 814) and ground 816 (only one called out in FIG. 8).

When a given transducer element 802 is to be used for blood flow sensing, the transducer selection switch 810 connected to the node A-I on one end of the given transducer element 802 is set to select the current source 814 and the transducer selection switch 810 connected to the node on the other end of the given transducer element 802 is configured to select ground 816. All nodes connected by a transducer element 802 to the node configured to select a current source 814 are also configured to select a current source 814. All nodes connected by a transducer element 802 to the node configured to select a ground are also configured to select ground 816. All of the connected current sources 814 are adjusted to deliver the same small voltage at the nodes A-I they are connected to. For example, if the transducer element 802*e* is to be used, then nodes B, D E, and H will be connected to current sources 814*b*, 814*d*, 814*e*, 814*h*, and nodes A, C, F, G, and I will be connected to ground 816. The connected current sources 814*b*, 814*e*, 814*d*, 814*h* will be adjusted so that the voltage at nodes B, E, D, and H will be the same. The control system 812 controls the voltage at the nodes, for example by:

selecting the desired node with a multiplexer 818;
measuring the voltage with an analog to digital converter (ADC) 820; and
adjusting the corresponding current source 814 to achieve the desired voltage.

In this configuration, the current through all transducer elements 802 connected to the given transducer element 802*e* will be zero. Therefore all current from the current source 814*e* connected to the given transducer element 802*e* will pass through the transducer element 802*e*. As both the voltage drop across and the current through the given transducer element 802*e* are known, the resistance can be determined and the corresponding temperature can be determined. Determination of the location of the openings or ports into the cavity (e.g., chamber or atrium) may be achieved by turning on all or at least some of transducer elements 802 sequentially, and determining the temperature by measuring a resistance of each of the transducer elements 802. The control system 812, or some other system, may produce a map of the temperature of the transducer elements 802, where the lower temperatures correspond to the openings or ports leading to veins or valves.

When a transducer element 802 is to be used for ablation, the transducer selection switch 810 connected to the node A-I on one end of the given transducer element 802 is set to select the current source 814 and the transducer selection switch 810 connected to the node A-I on the other end of the given transducer element 802 is configured to select a ground connection 816. All nodes A-I connected by a transducer element 802 to either end of the given transducer element 802 to be used for ablation are configured to select a current source 814. The current source 814 connected to the given transducer element 802 to be used for ablation is set to deliver sufficient power to the given transducer element 802 to raise its temperature to 50° C.-100° C., enough to cause non-blood tissue ablation. All of the other connected current sources 814 are adjusted to deliver current so that the voltages at the node A-I they are connected to is a percentage of the voltage at the node A-I connected to the given transducer element 802 being used for ablation. For example, if the transducer element 802e is to be used for ablation, then nodes B, C, D, E, H, and I will be connected to current sources 814b, 814c, 814d, 814e, 814h, 814i, and node A, F, and G will be connected to ground 816. The current source 814e connected to node E will be adjusted so that sufficient power is delivered to transducer element 802e to cause ablation. In doing so, a voltage will be generated at the node E. The current sources 814b, 814d, 814h connected to nodes B, D, and H are set to ensure the voltage at those nodes is, for example 66% of the voltage at node E. The current sources 814c, 814i connected to nodes C and I are set to ensure the voltages at those nodes is, for example 33% the voltage at node E. In doing do, the power delivered to all transducer elements 802 connected to nodes B, C, D, H, and I will be 11% of the power delivered to the given transducer element 802e, which is insufficient for ablation. It is possible to use different percentages for voltage values than specified herein.

While FIG. 8 shows one current source for each element, it is also possible to create a circuit that uses multiplexing to reduce the number of required current sources. Also, a circuit can be specified that uses voltage sources instead of current sources.

There are several ways to improve the accuracy in sensing the voltage drop across the transducer elements to improve accuracy of temperature measurement or flow sensing. One approach to achieve improved accuracy is to use four terminal sensing.

FIG. 6A shows a circuit 600a that implements four terminal sensing, according to one illustrated embodiment.

In FIG. 6A, a transducer element 602a is coupled to power leads 604a, 604b (collectively 604) to supply the current necessary to cause the transducer element 602a to heat sufficiently to be able to measure convective cooling. Measurement leads 606a, 606b (collectively 606) are used to measure the voltage across the transducer element 602a. Negligible current goes through measurement leads 606a, 606b and so there is no voltage drop over the length of the measurement leads 606.

In some configurations, being able to minimize the effect of lead resistance when measuring voltage across the transducer elements is possible without adding additional wires. FIG. 6B shows a circuit 600b that may implement such.

In temperature sensing or convective cooling sensing mode, leads 610a, 610b (collectively 610) are used to supply and sink the current necessary to cause transducer elements 612a-612e (collectively 612) to produce sufficient heat to be able to measure convective cooling. Leads 614a, 614b are used to measure the voltage across transducer element 612a. Leads 614b, 614c are used to measure the voltage across transducer element 612b. Leads 614c, 614d are used to measure the voltage across transducer element 612c. Leads 614d, 614e are used to measure the voltage across transducer element 612d. Leads 614e, 614f are used to measure the voltage across transducer element 612e. During ablation mode, leads 614a, 614b are used to supply the current to cause transducer element 612a to ablate the non-blood tissue, leads 614b, 614c are used to supply the current to cause the transducer element 612b to ablate, and so on.

FIG. 6C shows a circuit 600c according to another illustrated embodiment. The circuit 600c may minimize the effect of lead resistance when measuring voltage across the transducer elements without adding additional wires. As an example, the transducer element 622a between nodes J and O is being used for temperature, flow, or convective cooling sensing. The leads connected to nodes J and O supply the current to the transducer element 622a between the nodes. This causes a measurable voltage drop across the transducer element 622a between nodes J and O. The leads attached to nodes B, D, E, F, I, K, N, P, S, T, U, W are used to sense voltage at the respective nodes. The control system to which the leads are attached is configured so that there is negligible current flow through these leads, and negligible voltage drop across the leads. The leads attached to nodes A, C, G, H, L, M, Q, R, V, and X are actively driven and drive the nodes to a particular voltage. The control system adjusts the voltages at nodes A, C, G, H, and L so that the voltage measured at nodes B, D, E, F, I, and K are all measured to be equal. When this state occurs, the current between nodes E and D, E and B, E and F is negligible and therefore, the current between nodes E and J must be negligible, and node E will be at the same potential as node J. The control system adjusts the voltages at nodes X, R, V, M, and Q so that the voltage measured at nodes W, S, T, U, N, and P are all measured to be equal. When this state occurs, the current between nodes S and T, T and W, T and U is negligible and therefore, the current between nodes T and O must be negligible, and node T will be at the same potential as node O. The voltage drop across the element between nodes J and O is therefore equal to the difference between the voltage at node E and the voltage at node T.

Figure 9:
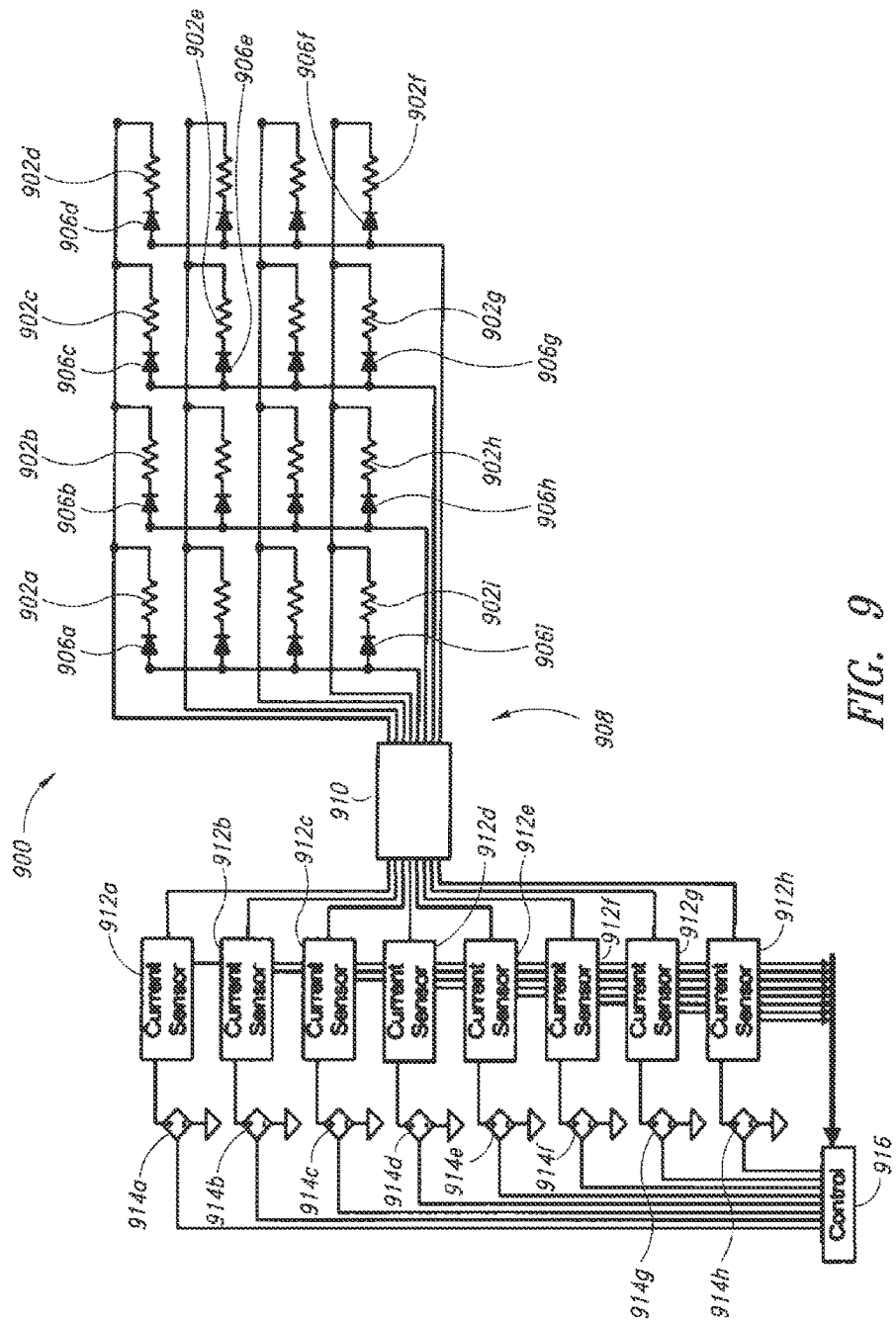
FIG. 9 is a circuit diagram of a third example of a system used for flow sensing, port location, and tissue ablation.

FIG. 9 shows an embodiment that reduces the number of control leads.

FIG. 9 shows a circuit 900 that includes a plurality of transducer elements 902a-902i (collectively 902, only nine called out in FIG. 9) which may form a one-, two-, or three-dimensional grid or array 904. A plurality of diodes 906a-906i (collectively 906, only nine called out in FIG. 9) or other non-linear devices or active devices are used to reduce the number of control leads 908. The leads 908 may be externally accessible from an exterior of a patient, for example via a cable 910 that extends through a lumen of a catheter or otherwise forms part of a catheter.

When this circuit 900 is not sensing or ablating, adjustable voltage sources 914a-914h (collectively 914, only eight called out in FIG. 9) are configured to reverse bias the diodes 906, so no current flows in the circuit 900. The circuit 900 may includes a plurality of current sensors 912a-912h (collectively 912), which couple signals indicative of sensed currents to a control system 916. In this example, the reverse biasing operation is achieved by setting voltage sources 914a-914d to positive voltage "h" and voltage sources 914e-914h to ground. When a transducer element 902 is to be used for flow sensing, temperature sensing, or ablation, the diode 906 that is in series with the given transducer element 902 is forward biased. This is achieved by setting the voltage source 914 that is connected to the given diode 906 to a positive voltage "g" that is greater than 0 and less than h, and setting the voltage source 914 that is connected to the given transducer element 902 to a positive voltage "f" which is greater than 0 and less than g and sufficient to forward bias the respective diode 906. For example, if the transducer element 902e is to be used for sensing or ablation, adjustable voltage source 914g should be set to g volts, adjustable voltage source 914h should be set to f volts, adjustable voltage sources 914a, 914c, 914d should be set to h volts, and adjustable voltage sources 914e, 914f, and 914h should be set to ground where 0<f<g<h. The particular values used for f, g, and h depend on such factors as the desired amount of heat from the transducer element 902 and the resistance of the transducer element 902. Since the forward voltage of a silicon diode changes about 2 mV/degC, the diodes 906 can also be used as temperature sensors.

In some embodiments, it is beneficial to ensure the entire medical treatment device is electrically insulated from the body. The reasons that this may be desirable are to prevent electrochemical activity from generating offset voltages, prevent leakage currents from affecting measurements and prevent gas bubble generation inside the blood stream.

Sensing Impedance Change

Measuring electrical impedance has been suggested as a way for determining when a catheter probe is in contact with the non-blood tissue of the heart wall. However, distinguishing non-blood tissue from blood using electrical impedance is problematic as the impedance is affected by many factors such as contact pressure and contact area. Also, the transducer element (e.g., electrode) may be in contact with many different materials, each of which has different impedance. However, using permittivity (also known as dielectric constant) measured over a range of frequencies can be used effectively to make the determination between blood and non-blood tissue.

As mentioned, material such as blood, muscle tissue, fat, fibrous material, and calcified tissue each has different impedance. However, in all the materials mentioned, except for blood (and other liquids such as urine) the permittivity drops with increasing frequency. For example, the conductivity of all those materials, including blood, stays nearly constant from DC to over 100 MHz. The permittivity of blood (and most other liquids in the body) is about the same at 1 KHz and 100 Khz, while in all other materials mentioned the dielectric constant drops by about a factor of 4, and typically by at least a factor of 10 between those two frequencies. Therefore, accurate discrimination between blood and non-blood tissue can be made by monitoring the ratio of the permittivity at 1 KHz to the value at 100 KHz. Table 1 and Table 2 show the change of Conductivity and Relative Permittivity with respect to frequency.

TABLE 1

Tissue Conductivity

| | Conductivity (S/m) | | | | |
|---|---|---|---|---|---|
| $\log_{10}$(Freq) | 3 | 5 | 6 | 7 | 8 |
| Blood | 0.7 | 0.7 | 0.7 | 1 | 1.49 |
| Fat | 0.025 | 0.025 | 0.03 | 0.04 | 0.06 |
| Muscle | 0.4 | 0.4 | 0.4 | 0.4 | 0.75 |
| Fibrous Material | 0.24 | 0.24 | 0.24 | 0.29 | 0.33 |

TABLE 1-continued

Tissue Conductivity

| | Conductivity (S/m) | | | | |
|---|---|---|---|---|---|
| Calcium | 0.08 | 0.08 | 0.1 | 0.12 | 0.17 |
| Vessel Wall | 0.58 | 0.58 | 0.58 | 0.67 | 0.83 |

TABLE 2

Tissue Relative Permittivity

| | Relative Permittivity | | | | |
|---|---|---|---|---|---|
| $\log_{10}$(Freq) | 3 | 5 | 6 | 7 | 8 |
| Blood | 4100 | 4000 | 2000 | 300 | 75 |
| Fat | 20000 | 100 | 50 | 30 | 12 |
| Muscle | 400000 | 10000 | 8000 | 200 | 70 |
| Fibrous Material | 2000 | 500 | 50 | 5 | 3 |
| Calcium | 10500 | 500 | 250 | 70 | 30 |
| Vessel Wall | 100000 | 5000 | 4000 | 100 | 30 |

FIGS. 10A-10D show examples of different ways that transducer elements to sense permittivity may be constructed. FIGS. 10A-10D show examples of various transducer elements which may be constructed using flexible printed circuit board substrates and/or materials. The resulting transducer elements may be affixed to a structure similar to the expandable frame 208 (FIG. 2) made from a material such as Nitinol. Alternatively, the resulting transducer elements may include PCB substrates of such a thickness that the PCB substrates may form the frame itself. The transducer elements could also be constructed using discrete components.

Figure 10A:
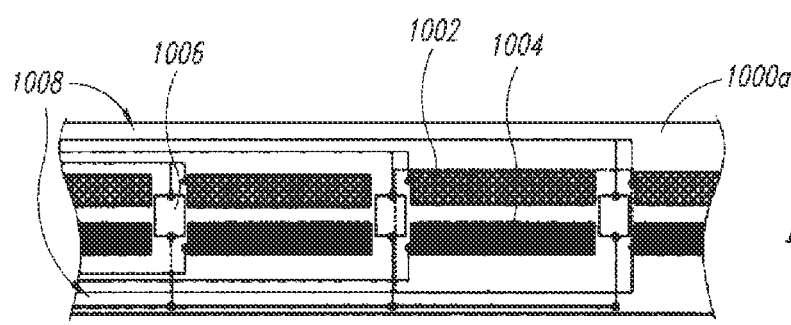
FIG. 10A is a top plan view of a structure having distinct permittivity sensor elements, temperature sensor elements and ablation elements, according to one illustrated embodiment.

FIG. 10A shows a flexible PCB substrate 1000a that carries permittivity sensor elements 1002 (only one called out in FIG. 10A) responsive to permittivity, ablation elements 1004 (only one called out in FIG. 10A) operable to ablate, and temperature sensor elements 1006 (only one called out in FIG. 10A) responsive to temperature. In the illustrated embodiment, the ablation elements 1004 and temperature sensor elements 1006 share some control leads 1008. Leads 1008 are coupled to a control system (not illustrated in FIG. 10B). It is also possible that each ablation elements 1004 and temperature sensor elements 1006 has separate control leads 1008 coupled to a control system (not illustrated in FIG. 10B).

Figure 10B:
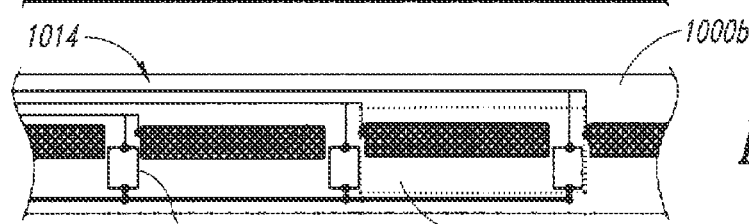
FIG. 10B is a top plan view of a structure having integrated permittivity sensor and ablation elements, according to one illustrated embodiment.

FIG. 10B shows a flexible PCB substrate 1000b that carries combined permittivity sensor and ablation elements 1010 (only one called out in FIG. 10B) that both responsive to permittivity and are operable to ablate tissue. The PCB substrate 1000b also carries separate temperature sensor elements 1012 (only one called out in FIG. 10B) that are responsive to temperature. Leads 1114 are coupled to a control system (not illustrated in FIG. 10B).

Figure 10C:
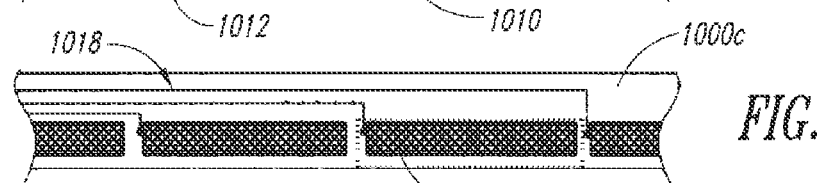
FIG. 10C is a top plan view of a structure having integrated permittivity sensor and ablation elements, according to another illustrated embodiment.

FIG. 10C shows a flexible PCB substrate 1000c that carries combined permittivity and ablate elements 1016 (only one called out in FIG. 10O) that both are responsive to permittivity and are operable to ablate non-blood tissue. Each of the combined permittivity and ablate elements 1016 has a respective lead, collectively 1018, extending to a control system (not shown in FIG. 10C). An example of a circuit used to control and activate the combined permittivity and ablate elements 1016 is shown in FIG. 11.

Figure 10D:
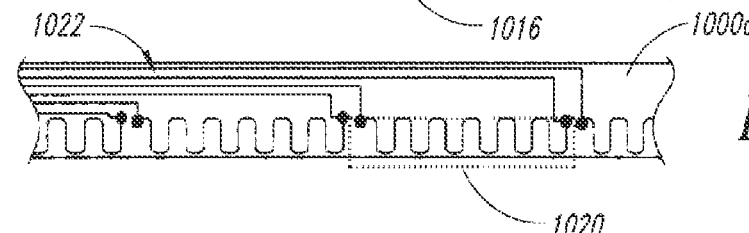
FIG. 10D is a top plan view of a structure having integrated permittivity and temperature sensor and ablation elements, according to one illustrated embodiment.

FIG. 10D shows a flexible PCB substrate 1000d that carries combined permittivity sensor, temperature sensor and ablation elements 1020 that are responsive to permittivity, responsive to temperature and operable to ablate non-blood tissue. Each of the combined elements is coupled by a respective lead, collectively 1022, to a control system (not illustrated in FIG. 10D). Such an embodiment can be built using a printed circuit board with copper traces that do not have a surface insulation. The temperature sensing and ablation can be controlled as previously described in reference to FIG. 7. The permittivity sensing can be controlled as will be described with reference to FIG. 11.

Figure 11:
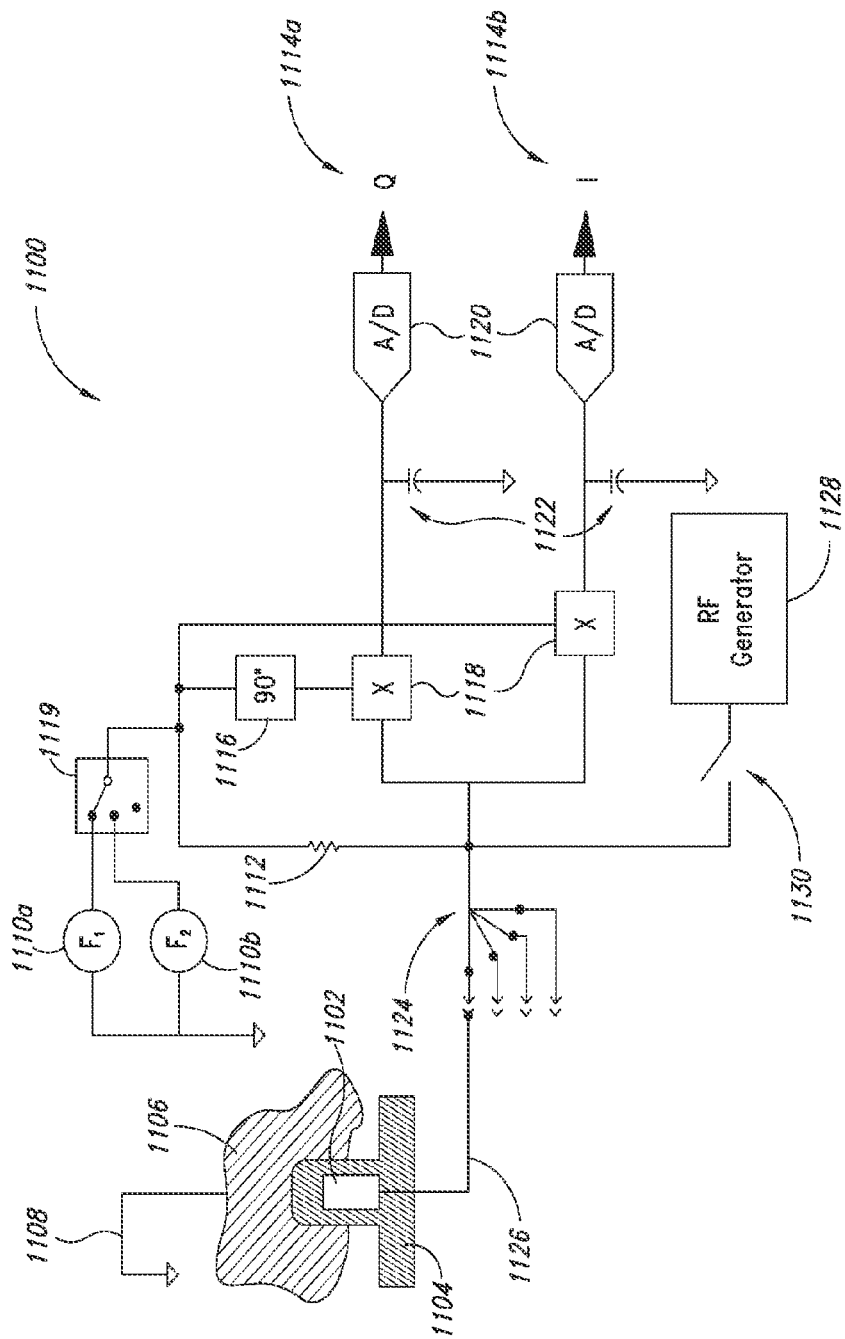
FIG. 11 is a circuit diagram of an example of a system used for permittivity sensing, port location, and tissue ablation.

FIG. 11 shows a circuit 1100 that can be used to distinguish blood from non-blood tissue by detecting the change in permittivity, according to one illustrated embodiment.

A transducer element 1102 carried on a PCB substrate 1104 is in physical contact with a bodily material 1106 (non-blood tissue or blood). The bodily material 1106 is electrically grounded to a same return path 1108 as the circuit 1100. Instead of a return path, a ground electrode adjacent to the transducer element (e.g., electrode) 1102 can be used. An alternate embodiment may be to use a balanced pair of electrodes with equal but opposite phase signals relative to ground. Such a configuration increases immunity to electrical noise. When frequency $F_1$ or $F_2$ is fed to transducer element 1102 from oscillators 1110a, 1110b via a resistor 1112 the phase shift of the signal caused by the dielectric constant of the bodily material 1106 can be measured by a phase meter. The permittivity is the tangent of the phase shift. For better noise immunity both the in-phase component and the out-of-phase, or quadrature, are measured (outputs 1114a, 1114b) then divided to determine the phase shift. The in-phase and out-of phase components are measured by multiplying the voltage signal on transducer element 1102 with the driving signal and with the driving signal phase shifted by 90 degrees using phase shifter 1116 and multipliers 1118. A selector 1119 may be used to selectively switch between coupling the frequencies $F_1$, $F_2$, or no frequency.

A pair of analog-to-digital converters (ADC) 1120 are used to digitize the results, after low pass filtering by capacitor 1122. If desired, the complete operation can be performed digitally by digitizing the signal from the transducer element 1102, since the highest frequency is relatively low. A separate circuit can be used for each transducer element 1102 or a selector 1124 (also known as multiplexer or analog switch) can connect the same circuit to multiple transducer elements 1102 in rapid succession. The time needed for an accurate measurement is typically several milliseconds; therefore even a large grid or array of transducer elements 1102 can be mapped quickly. A same lead 1126 can also be used to feed current for RF ablation using ablation energy source 1128 and a switch 1130. Alternatively a different power source, such as a DC current source, could be connected and provide a voltage and current for directly causing the transducer element 1102 to produce a sufficient amount of heat to cause ablation.

Sensing Force

Another method of distinguishing between non-blood tissue and blood is to measure a force being exerted inwardly on one or more transducer elements mounted or otherwise carried by an expandable frame (e.g., expandable frame 208 of FIG. 2). As an example of this approach, the transducer elements may take the form of an array of force sensors, for example force sensing pads. A polymeric piezoelectric material, such as PVDF, may be used as a force sensing element and two or more force sensing elements may be combined to form a force sensing grid. Such force sensing elements are already commercially available, such as Ktech part number MP-25-04-PL (from www.ktech.com). These PVDF based force sensing pads are very thin, flexible, have high output and are easy to integrate into a flexible printed circuit board. Liquids, such as blood, create very little resistive force when the expandable frame forces the force sensor transducer elements outward to the non-blood tissue that forms the interior surface of the cavity being mapped. The force sensor transducer elements located proximate to the openings or ports will be subject to less force than those proximate to the non-blood tissue. The differing force distribution across the force sensor transducer elements enables the location of the openings or ports to be determined.

FIGS. 12A-12C show examples of different ways the force sensor transducer elements may be constructed using flexible printed circuit board substrates. Force sensor transducer elements may be affixed to a structure similar to previously described expandable frames (e.g., expandable frame 208 of FIG. 1) made from a material such as Nitinol. Alternatively, the PCB substrate may be of such a thickness that the PCB substrate can be the frame itself. The transducer elements could also be constructed using discrete components.

FIG. 12A shows a flexible printed circuit board substrate 1200a that carries separate force sensor transducer elements 1202 (only one called out in FIG. 12A) responsive to force, temperature sensor transducer elements 1204 (only one called out in FIG. 12A) responsive to temperature, and ablation transducer elements 1206 (only one called out in FIG. 12A) operable to ablate non-blood tissue. The various transducer elements 1202, 1204, 1206 share a common ground 1208. The ablation and temperature sensor transducer elements 1206, 1204, respectively, share a common control lead 1210. Control leads 1210 are coupled to a control system (not shown in FIG. 12A). The preferred force sensor transducer element 1202 is a polymeric piezoelectric material. An example of a circuit that can be used to control and monitor such force sensor transducer elements 1202 is shown in FIG. 13.

FIG. 12B shows a flexible printed circuit board substrate 1200b that carries separate force sensor transducer elements 1222 (only one called out in FIG. 12B) responsive to force and elements with a combined temperature sensor and ablation transducer elements 1224 (only one called out in FIG. 12B). Each of the transducer elements 1222, 1224 has respective leads, collectively 1226, coupled to a control system (not shown in FIG. 12B). The combined temperature sensor and ablation transducer elements 1224 can be controlled in the same way as described for the embodiment of FIG. 7. The force sensor transducer element 1222 can be controlled and monitored as described herein with reference to FIG. 13.

FIG. 12C shows a flexible printed circuit board substrate 1200c that carries force sensor transducer elements 1232 (only one called out in FIG. 12C) responsive to force, and combined or integrated temperature sensor and ablation transducer elements 1234 (only one called out in FIG. 12C) responsive to temperature and operable to ablate non-blood tissue. The combined temperature sensor and ablation transducer elements 1234 are distinct from the force sensor transducer elements 1232. Each of the various types of transducer elements 1232, 1234 has respective leads, collectively 1236, coupled to a control system (not shown in FIG. 12C) possibly via a multiplexer (not shown in FIG. 12C). The combined temperature sensor and ablation transducer elements may be controlled in the same way as previously discussed with reference to FIG. 7.

Figure 13:
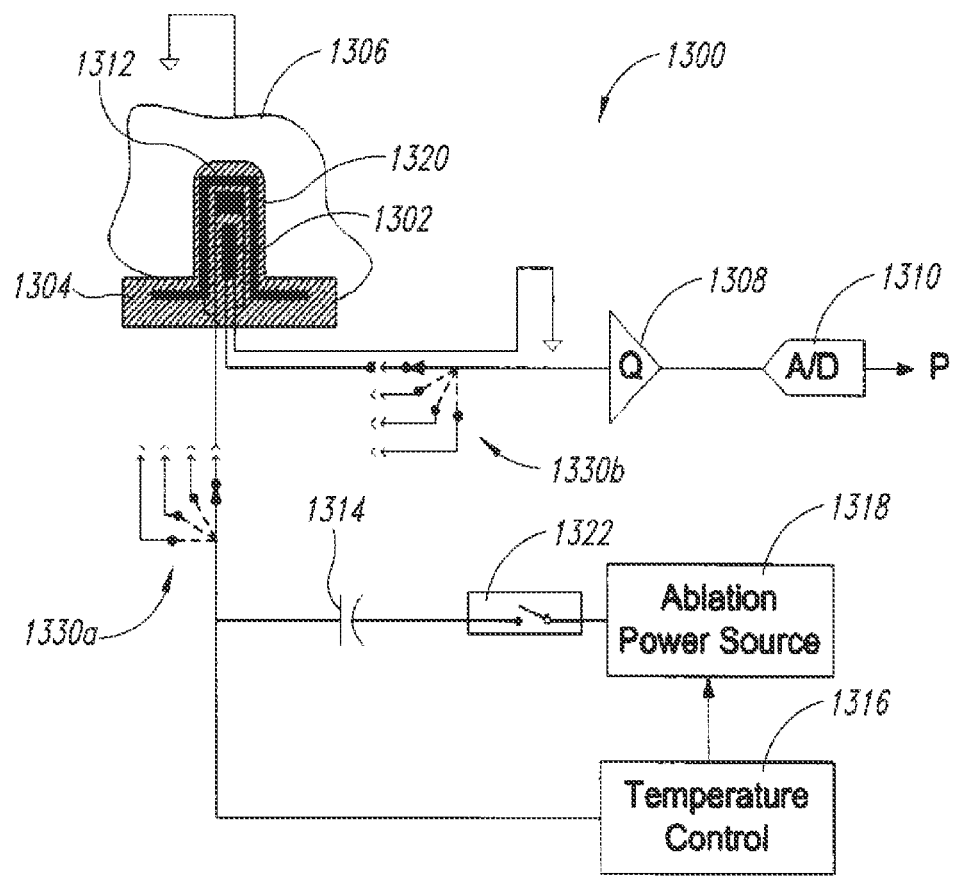
FIG. 13 is a circuit diagram of an example of a system used for force sensing, port location, and tissue ablation.

FIG. 13 shows an embodiment of a circuit 1300 used to sense the forces the force sensor transducer elements (e.g., FIGS. 12A-12C) sense, according to one illustrated embodiment.

A force is exerted on a force sensor transducer element 1302 carried by a flexible PCB substrate 1304, by a bodily material 1306, for example blood or non-blood tissue.

A charge amplifier 1308 converts an output of the force sensor transducer element 1302 to a voltage which is digitized by an analog-to-digital (ADC) converter 1310. This voltage is proportional to the force exerted on the force sensor transducer element 1302 by the bodily material 1306, and the output may be indicative of a pressure. An ablation transducer element (e.g., electrode) can be used for temperature monitoring, as explained earlier, or a separate temperature sensor 1312 can be used. A capacitor 1314 can be used to isolate the RF from the DC current used for temperature sensing. Temperature sensing may be used by a temperature controller 1316 to control an ablation power source 1318 to cause an ablation transducer element 1320 to produce an appropriate amount of ablation (e.g., controlling time, temperature, current, power, etc.). A switch 1322 or valve may selectively couple the ablation power source 1318 to the ablation transducer element 1320.

When a polymeric piezoelectric material is used as the force sensor transducer element 1302, it is important to ensure the force sensor transducer element 1302 is sufficiently electrically insulated to eliminate any leakage current. A possible insulating material to use is silicone. Also, integrating an amplifier near the piezoelectric force sensor transducer element 1302 may improve the circuit performance and may make the circuit 1300 less susceptible to leakage current.

Although this circuit 1300 uses multiplexing via connectors 1330a, 1330b to measure the force exerted on the elements, it is also possible to forgo multiplexing and have a circuit dedicated for each element, or a combination of both techniques.

Note that the same piezoelectric sensing grid can also be used in alternate ways to differentiate non-blood tissue from blood. For example, it can be used as an ultrasonic transmitter and receiver to differentiate based on reflection or on damping coefficient.

Frame

The frame provides expansion and contraction capabilities for the component of the medical device (e.g., grid or array of transducer elements) used to distinguish between blood and non-blood tissue. The transducer elements used to sense a parameter or characteristic to distinguish between blood and non-blood tissue may be mounted or otherwise carried on a frame, or may form an integral component of the frame itself. The frame may be flexible enough to slide within a catheter sheath in order to be deployed percutaneously. FIG. 2, discussed previously, showed one embodiment of such a frame. Additional embodiments of frames are shown in FIGS. 14A, 14B, 15A, 15B, 15C, 16A and 16B.

Figures 14A, 14B:
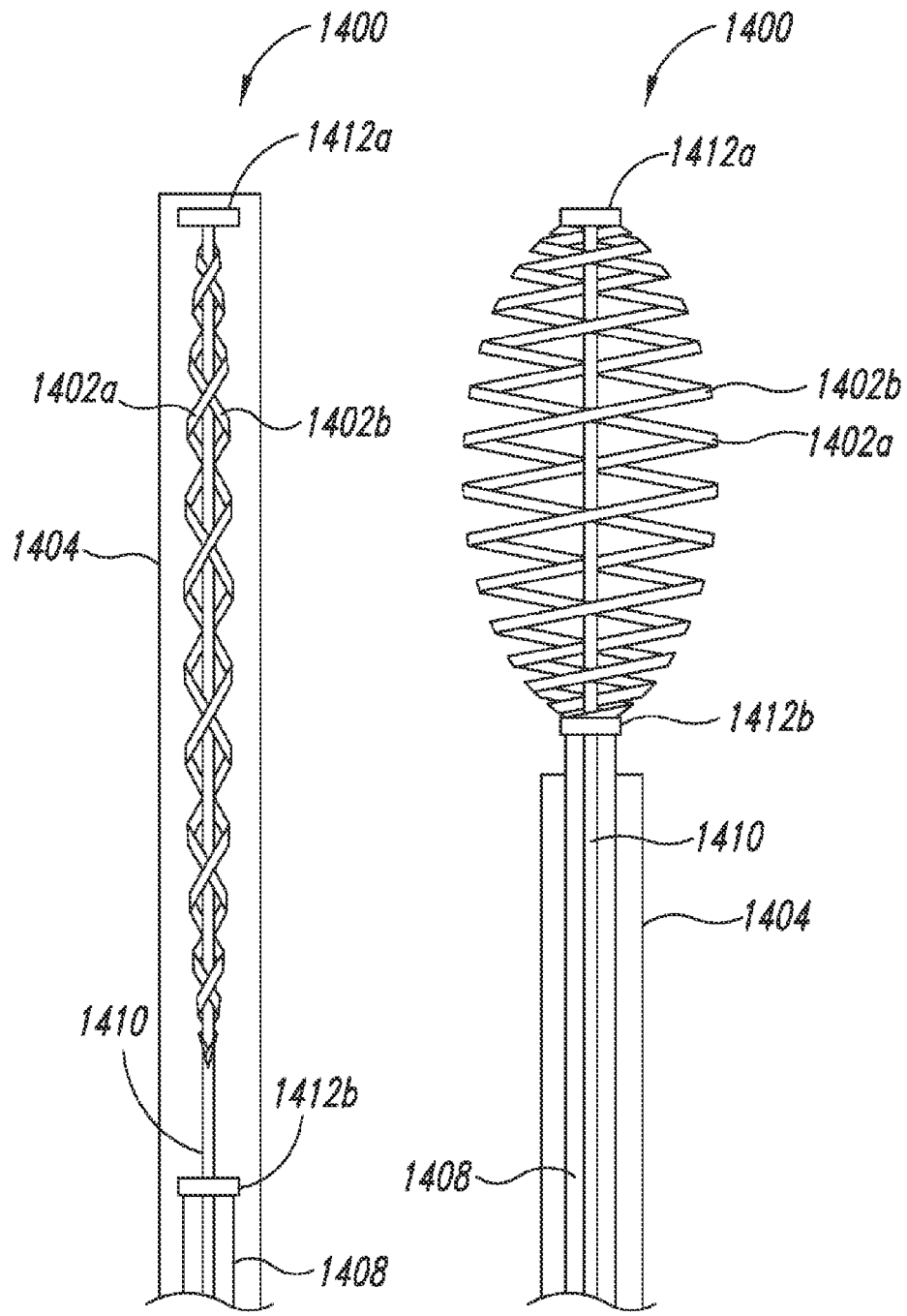
FIG. 14A is an example of a frame using multiple helix shaped members.
FIG. 14B is an example of a frame using multiple helix shaped members.

FIG. 14A shows a frame 1400 made from a number of helical members 1402a, 1402b (collectively 1402) in an unexpanded configuration and positioned within a catheter sheath 1404 of a catheter 1408. FIG. 14B shows the frame 1400 extended outside of the catheter sheath 1404 and in an expanded configuration.

The helical members 1402 may be disposed about a shaft 1410. The helical members 1402 may be positioned between opposing stops 1412a, 1412b, which engage the ends of the helical members 1402 to cause expansion. While two helical members are shown, some embodiments may employ a greater or fewer number of helical members 1402.

The frame 1400 is expanded by retracting a shaft 1410. Retracting the shaft 1410 causes the midpoint of the helical members to be forced outward and move toward the interior surface of the cavity in which the frame is positioned. FIG. 14B shows that some of the helical members 1402 are oriented in a clockwise direction and others are oriented in a counter clockwise direction. The opposing directions cause the helical members 1402a, 1402b to cross over and form a grid.

The helical members 1402 may be constructed of many different types of material including solid wire (such as stainless steel), hollow tube, carbon fiber, or a flexible PCB with a fibreglass or Nitinol backing. The helical members 1402 may form an integral component of the sensing and ablation transducer elements. FIG. 4 provided several example of how elements could be constructed from solid wire, hollow tube, carbon fiber, or flexible PCB. When the transducer elements form an integral component of the frame, the material to be used for the frame requires proper mechanical and electrical properties. If the device is distinguishing between blood and non-blood tissue using flow sensing, the material used for the helical members 1402 preferably has a significant change in resistance with temperature that is independent of helical members 1402 deformation. Also, a resistance of several ohms per centimeter or higher is preferable as it will reduce the amount of current needed to heat the transducer element. The helical members 1402 may also act as a support for a secondary assembly that carries the sensing and ablation transducer elements. An example of this is a stainless steel or Nitinol structure used to expand transducer elements made with a flexible PCB substrate.

FIGS. 15A-15C show a frame 1500, according to another illustrated embodiment.

The frame 1500 includes a single helical member 1502, a plurality of ribs 1504, and a shaft 1506, oriented approximately parallel to a longitudinal axis of a catheter 1508. The sensor and ablation transducer elements are located along the helical member 1502 and ribs 1504.

FIG. 15A shows the frame 1500 in its unexpanded or contracted configuration, positioned within a catheter sheath 1510 of the catheter 1508. In the unexpanded or contracted configuration, the ribs 1504 are compressed against the shaft 1506 and the single helical member 1502 is wound around the ribs 1504. The catheter sheath 1510 is inserted partially into the lumen, cavity, chamber or atrium that the device is to operate in. The frame 1500 is then pushed out of the sheath 1510 into the chamber and then expanded.

FIG. 15B shows the frame 1500 in a partially expanded configuration. The frame 1500 is expanded by first unwinding the helical member 1502. The shaft 1506 is rotated, which causes the helical member 1502 to unwind and expand outward from the shaft 1506.

FIG. 15C shows the frame 1500 in a fully expanded configuration. The frame 1500 is fully expanded by retracting the shaft 1506, which causes the ribs 1504 to bow outwards and move both the helical member 1502 and ribs 1504 to be proximate to the non-blood tissue that forms the interior surface of the chamber. The ribs 1504 and helical member 1502 may only be physically attached at the proximal and distal ends of the ribs 1504 and helical member 1502, or the ribs 1504 may have loops spaced along their length through which the helical member 1502 slides.

There are several variations on the example shown in FIGS. 15A-15C. These include a frame in which the helical member is inside the ribs, and pushes the ribs outward. Alternatively, a frame may include a helical member that is positioned inside the ribs, and the ribs are only attached at the proximal or distal end.

The same principles regarding construction and composition of the ribs described for the frame 1400 of FIGS. 14A and 14B may be applied to the frame 1500 of FIGS. 15A-15C.

FIGS. 16A and 16B show an embodiment a frame 1600 made using one or more inflatable members 1602. The particular inflatable member 1602 shown is approximately spherical in shape, although it is possible to construct a frame using inflatable members that are oblong as well.

FIG. 16A shows the frame 1600 in an inflated or expanded configuration. FIG. 16B shows a cross section of the frame 1600. The preferred method of expanding this frame 1600 is to inflate via one or more ports 1604 with a fluid. A fluid, such as saline, that is not dangerous if inadvertently released into the body may be particularly suitable. The port 1604 may be fluidly communicatively coupled to source of fluid, for example via one or more lumens of a catheter 1606. The source of fluid may be pressurized. The inflatable member 1602 may be folded inside a catheter sheath 1608 for percutaneous or intravascular delivery. The inflatable member 1602 may be withdrawn or pushed from the catheter sheath 1608 when in a desired position in the bodily organ.

This inflatable member may have one or more passages, collectively 1610, (only three called out in FIGS. 16A and 16B) opening to the exterior surface 1612. The passages 1610 may provide fluid communication through the inflatable member 1602. For example, the passages 1610 may connect to a hollow interior cavity 1614. These passages 1610 allow blood to flow through the frame 1600 even when the frame 1600 is inflated sufficiently to be in contact with the interior surface of the lumen, cavity, chamber or atrium in which the frame 1600 is located. Thus, blood may flow from a downstream side or position, to and open stream side [D1] or position, relative to the position of the frame 1600, even when inflated and in the expanded configuration. Such advantageously prevents occlusion.

An advantageous design feature when building an inflatable member that has interior structures, such as blood flow passages 1610 or an inner cavity 1614 is that the walls that form those interior structures should be reinforced to prevent the wall from collapsing or buckling. Such reinforcement can be accomplished in variety of ways. For example, by creating the inner walls using much thicker material, creating ribbed walls with alternating thinner or thicker sections, collectively 1616, (only three called out in FIG. 16B), or reinforcing the walls with spring like wires.

An inflatable frame 1600 as described may be created using a material such as latex. This device may be used as a supporting frame for elements, for example constructed using flexible printed circuit boards.

Joint Assembly

Several of the frames discussed in the preceding section employ joints where transducer elements cross over one another. FIGS. 17A-17E and FIGS. 18A-18B show several examples of different structures that can be used.

Figure 17A:
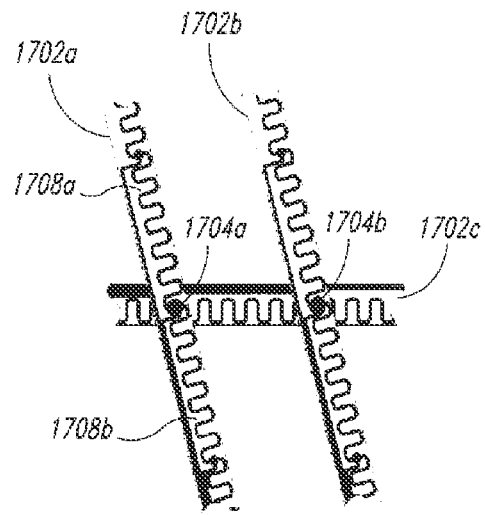
FIG. 17A is a top plan view of a joint assembly structure, according to one illustrated embodiment.

FIG. 17A shows several strips 1702a-1702c (collectively 1702) of flexible printed circuit board substrate at different orientations to one another. Such strips 1702 may be used to build the ribs, struts, or frame members mentioned previously. Where the strips 1702 cross, they may be joined by a hinge 1704a, 1704b (collectively 1704) that attaches both strips 1702. The hinge 1704 may, for example extend through both strips 1702. The 1702 strips are still able to swivel around the hinge point. The preferred place to join the strips 1702 is at the connecting points between transducer elements 1708a,1708b (collectively 1708, only two called out in FIG. 17A). If the transducer elements 1708 are designed to share leads, the hinge can be used to electrically connect the transducer elements 1708 that have an end coincident with the joint. Alternatively the transducer elements 1708 may be electrically insulated from the hinge 1704 with no electrical contact points between the strips 1702. The transducer elements 1708 between the hinges 1704 may be used to distinguish between blood and non-blood tissue and/or to ablate. Leads may extend along each strip 1702 back to the catheter (not shown in FIG. 17A) and to a control system (not shown in FIG. 17A).

Figure 17B:
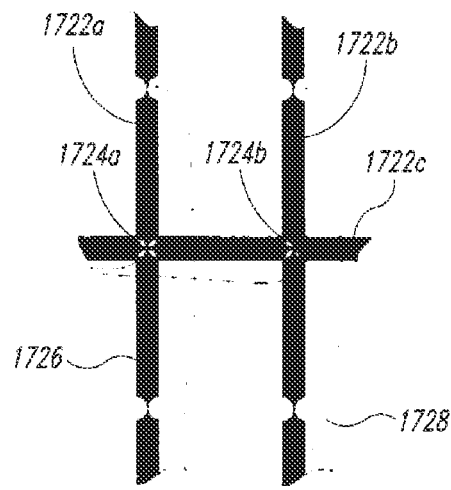
FIG. 17B is a top plan view of a joint assembly structure, according to another illustrated embodiment.

FIG. 17B shows several strands 1722a-1722c (collectively 1722) of carbon fiber at different orientations to one another. Such strands 1722 may be used to build the ribs, struts, or frame members mentioned previously. Where the strands 1722 cross, the carbon fiber strands 1722 are pinched or crimped 1724a, 1724b (collectively 1724) together, for example by means of a crimping mechanism. The crimping mechanism may be made from materials such as carbon fibre, carbon paste (cured by heating) metal, or glue. Pinching the carbon fibre together at the joint enables the strands to swivel about the joint. The carbon fibre between each connecting point can be used as a transducer element 1726 (only one called out in FIG. 17B) to sense flow, sense temperature and/or to ablate. A lead 1728 (only one called out in FIG. 17B) can be connected at each joint to control the transducer elements 1726 as shown by the circuit 800 of FIG. 8.

Figure 17C:
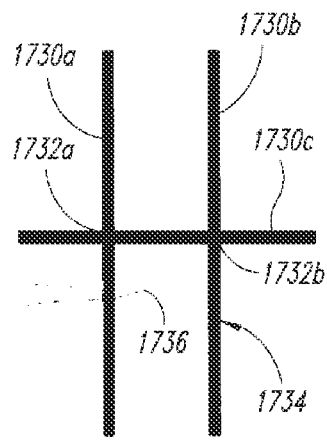
FIG. 17C is a top plan view of a joint assembly structure, according to another illustrated embodiment.

FIG. 17C shows several wires or hollow tubes 1730a-1730b (collectively 1730) made of material such as stainless steel or Nitinol, at different orientations from one another. Such wires or tubes 1730 may be used to build the ribs, struts, or frame members mentioned previously. Where the wires or tubes 1730 cross, they are connected at joints or connection points 1732a, 1732b (collectively 1732) for example by being fused together using spot or laser welding. The wire or tube between each connecting point can be used as a transducer element, collectively 1734 (only one called out in FIG. 17C), to sense flow, sense temperature and/or to ablate. A lead, collectively 1736 (only one called out in FIG. 17C), can be connected at each joint or connection point 1732 to control the transducer elements 1734 as shown by the circuit in FIG. 8.

Figure 17D:
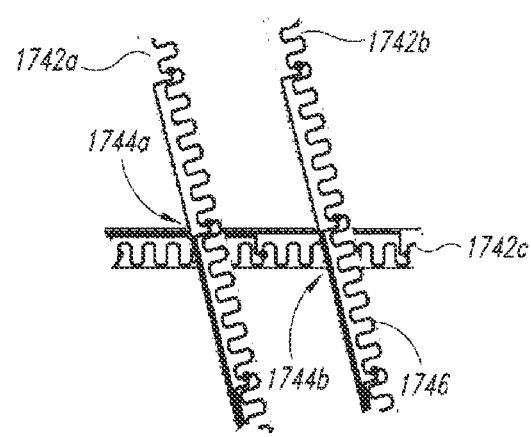
FIG. 17D is a top plan view of a joint assembly structure, according to another illustrated embodiment.
Figure 17E:
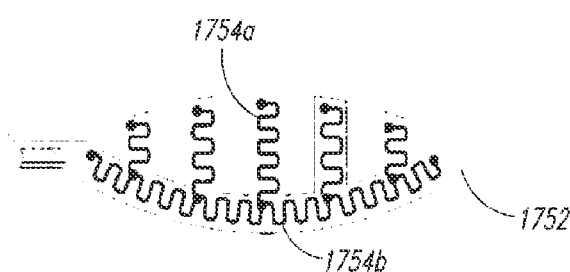
FIG. 17E is a top plan view of a joint assembly structure, according to another illustrated embodiment.

FIG. 17D shows several strips 1742a-1742c (collectively 1742) of flexible printed circuit board substrate at different orientations to one another. Such strips 1742 may be used to build the ribs, struts, or frame members mentioned previously. Where the strips 1742 cross 1744a, 1744b (collectively 1744), they are not mechanically joined, but allowed to slide over top of each other. Since a fixed hinge point does not exist in the configuration, it is necessary to be able to determine where the strips 1742 cross when the frame is in the expanded configuration inside a body lumen, cavity, chamber or atrium in order to properly determine the location of openings or ports of the lumen, cavity, chamber or atrium. One method of doing this is to make use of the heating and temperature sensing capabilities of the transducer elements 1746 (only one called out in FIG. 17D). Each transducer element 1746 should be heated slightly in turn (such as several degrees above blood temperature) while other transducer elements 1746 are sensing temperature. If the transducer element 1746 being heated is located at a crossing point, a different transducer element 1746 sensing temperature, but also located at the same crossing point will sense a temperature increase. All or most pairs of transducer elements 1746 that cross may be determined using such an approach FIG. 17E shows a flexible printed circuit board substrate 1752 in a leaf shape. Such a PCB substrate 1752 is used to cover one portion of the interior surface of the body cavity. Multiple such PCB substrates may be joined together as shown in FIG. 2, to cover at least a significant portion of the surface of a lumen, cavity, chamber or atrium. These PCB substrates may surround a frame that is used to push them outward and proximate to the surface. The PCB substrates may overlap. Overlapping transducer elements 1754a, 1754b (collectively 1754, only two called out in FIG. 17E) may be determined using the method described for the embodiment of FIG. 17D.

Figure 18A:
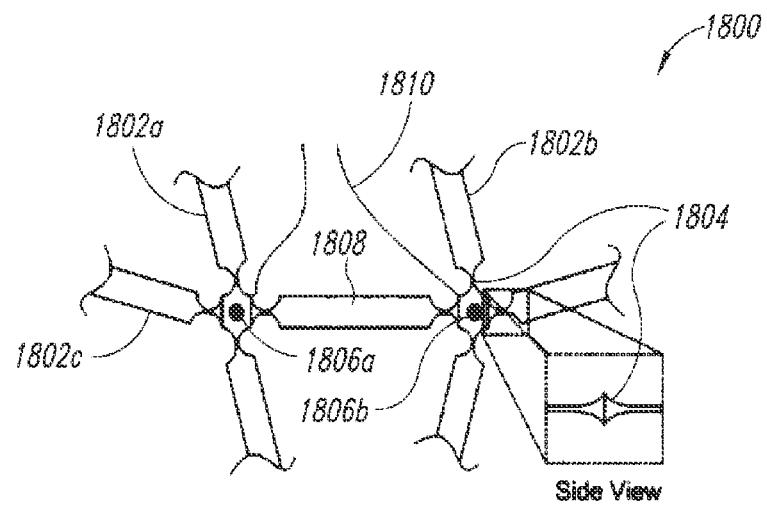
FIG. 18A is a top plan view of a joint assembly structure, according to another illustrated embodiment.

FIG. 18A shows a frame 1800 formed from metal strips 1802a-1802c (collectively 1802) formed to have flexure points 1804. Such strips 1802 may be used to build the ribs, struts, or frame members mentioned previously. The ribs, struts, or frames have crossing points 1806a, 1806b (collectively 1806). At the crossing points 1806 the metal strips 1802 are fused together using spot welding. The metal strips 1802 are formed to have a flexure 1804 on either side of the crossing point 1806. The flexure 1804 enables the strips 1802 to bend which may be beneficial for the expansion and contraction of the frame 1800. A portion of the strip 1802 between each connecting or crossing point 1806 can be used as a transducer element 1808 (only one called out in FIG. 18A) to sense flow, sense temperature and/or to ablate non-blood tissue. A lead 1810 (only one called out in FIG. 18A) can be connected at each joint to control the transducer elements 1808 as shown by the circuit in FIG. 8.

Figure 18B:
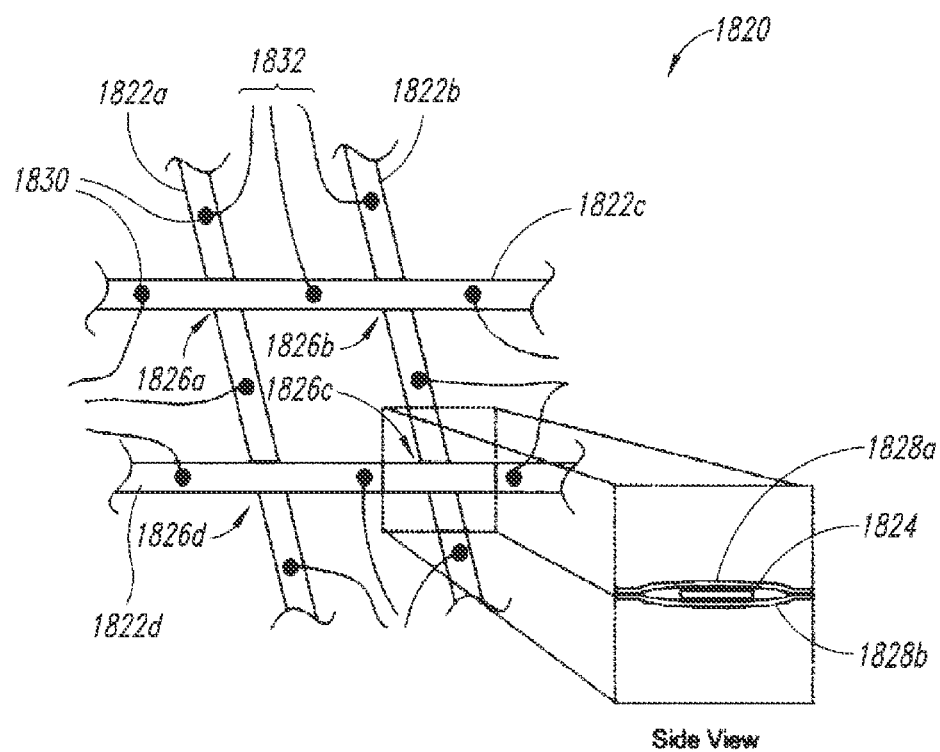
FIG. 18B is a top plan view of a joint assembly structure, according to another illustrated embodiment.

FIG. 18B shows a frame 1820 formed from metal strips 1822a-1822d (collectively 1822) formed to have slots 1824 (only one illustrated). Such strips 1822 may be used to build the ribs, struts, or frame members mentioned previously. The ribs, struts, or frames have crossing points 1826a-1826d (collectively 1826). At the crossing point 1826 of two strips 1822, one of the strips has a slot 1824 and the other strip 1822 slides through the slot 1824. The slot 1824 may be formed in a strip 1822 by joining two thin strips 1828a, 1828b by spot welds 1830 (only two called out in FIG. 18B). It is possible to connect the control leads 1832 to the spot welds 1830 which are located between the crossing points 1826 and use the portions of the strips 1822 between each connecting or crossing point 1826 as a transducer element to sense flow, sense temperature and/or ablate non-blood tissue. However, this method will require approximately 40% more wires than connecting the control leads at the crossing points.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the invention can be modified, if necessary, to employ systems, circuits and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all medical treatment devices in accordance with the claims. Accordingly, the invention is not limited by the disclosure, but instead its scope is to be determined entirely by the following claims.

The invention claimed is:

1. A method of operating a medical system, the method executed by a computing system communicatively connected to the medical system and comprising:
   causing transducer electrodes to sense at least in part a physical interior surface of a tissue wall of a bodily organ, the physical interior surface interrupted by one or more ports in fluid communication with the bodily organ, the transducer electrodes carried by a frame of a medical device of the medical system, the frame located in at least a portion of the bodily organ, and the causing the transducer electrodes to sense including causing each of the transducer electrodes to sense at least one characteristic indicative of whether a fluid or non-fluid tissue is present and not indicative of a flow of the fluid in the bodily organ;
   determining a position of the medical device in the bodily organ at least by executing a mapping process to map the bodily organ, the mapping process including locating one or more positions of the one or more ports at least by computationally discriminating between the fluid and the non-fluid tissue based at least in part on the at least one characteristic sensed by at least some of the transducer electrodes; and
   causing at least one display of the medical system to display output from the mapping process.

2. The method of claim 1 wherein the medical system includes an ablation source, the ablation source coupled to each of at least one transducer element of the medical system, the method further comprising:
   causing the ablation source and the at least one transducer element to ablate a portion of the non-fluid tissue in the bodily organ.

3. The method of claim 2 wherein the bodily organ is a heart, the fluid is blood, and the non-fluid tissue is a non-blood tissue, the method further comprising:
   causing each of at least one of the transducer electrodes to sense an electrical potential of the non-blood tissue in the heart at least once after the ablating; and
   causing production of an indication based on the sensed electrical potential of the non-blood tissue indicative of whether the ablating was successful.

4. The method of claim 1 wherein the at least one characteristic includes a permittivity of the fluid or the non-fluid tissue at each of a plurality of frequencies.

5. The method of claim 1 wherein the determining of the position of the medical device in the bodily organ includes providing information indicative of a three-dimensional pose of the medical device with respect to at least part of the bodily organ.

6. A method of operating a medical system including a device locatable in at least a portion of a heart, the device including transducer electrodes, the method executed by a computing system communicatively connected to the medical system, and the method comprising:
   causing the transducer electrodes to sense at least in part a physical interior surface of a tissue wall of the heart, the physical interior surface interrupted by one or more ports in fluid communication with the heart, the causing the transducer electrodes to sense including causing each of the transducer electrodes to sense at least one characteristic indicative of whether blood or non-blood tissue is present and not indicative of a flow of the blood in the heart, and the causing the transducer electrodes to sense including causing each of the transducer electrodes to sense electrical potential of the non-blood tissue in the heart;

determining a position of the device in the heart at least by executing a mapping process to map the heart, the mapping process including locating one or more positions of the one or more ports at least by computationally discriminating between the blood and the non-blood tissue based at least in part on the at least one characteristic sensed by at least some of the transducer electrodes; and providing information indicative of a position of the device in the heart and an indication based on the electrical potential of the non-blood tissue sensed by one or more of the transducer electrodes.

7. The method of claim 6, wherein the medical system includes an ablation source coupled to each of at least one transducer element of the medical system, the method further comprising:

causing the ablation source and the at least one transducer element to ablate a portion of the non-blood tissue in the heart.

8. The method of claim 7, further comprising:

causing one or more of the transducer electrodes to sense electrical potential of the non-blood tissue at least once after the ablating; and producing an indication of whether the ablating was successful based on the electrical potential of the non-blood tissue sensed by the one or more of the transducer electrodes.

9. The method of claim 6 wherein the computationally discriminating between the blood and the non-blood tissue is not based on a velocity or an acceleration of a flow of blood in the heart.

* * * * *